(12) United States Patent
Corbett et al.

(10) Patent No.: US 8,921,040 B2
(45) Date of Patent: Dec. 30, 2014

(54) METHOD AND APPARATUS FOR CONDUCTING AN ASSAY

(75) Inventors: John Corbett, Vaucluse (AU); John Corbett, Sr., Paradise Point (AU)

(73) Assignee: Pyrobett Pte Ltd., Singapore (SG)

( * ) Notice: Subject to any disclaimer, the term of this patent is extended or adjusted under 35 U.S.C. 154(b) by 0 days.

(21) Appl. No.: 13/386,834

(22) PCT Filed: Jul. 29, 2010

(86) PCT No.: PCT/AU2010/000953
§ 371 (c)(1),
(2), (4) Date: Apr. 23, 2012

(87) PCT Pub. No.: WO2011/011823
PCT Pub. Date: Feb. 3, 2011

(65) Prior Publication Data
US 2012/0282708 A1       Nov. 8, 2012

(30) Foreign Application Priority Data

Jul. 29, 2009 (AU) .................................. 2009903546

(51) Int. Cl.
| | | |
|---|---|---|
| C12Q 1/68 | (2006.01) | |
| G01N 35/00 | (2006.01) | |
| G01N 33/53 | (2006.01) | |
| G01N 33/58 | (2006.01) | |
| B01L 3/00 | (2006.01) | |

(52) U.S. Cl.
CPC ...... *G01N 35/00029* (2013.01); *G01N 33/5308* (2013.01); *G01N 33/582* (2013.01);
(Continued)

(58) Field of Classification Search
None
See application file for complete search history.

(56) References Cited

U.S. PATENT DOCUMENTS

| 4,883,750 A | 11/1989 | Whiteley et al. |
| 5,639,428 A * | 6/1997 | Cottingham .................. 422/112 |

(Continued)

FOREIGN PATENT DOCUMENTS

| EP | 1324042 | 7/2003 |
| WO | 89/09283 | 10/1989 |

(Continued)

OTHER PUBLICATIONS

Zackrisson, A. et al., "Identification of CYP2D6 alleles by single nucleotide polymorphism analysis using pyrosequencing" Eur. J. Clin. Pharmacol. (2003) 59:521-526.*

(Continued)

*Primary Examiner* — Bao Thuy L Nguyen
*Assistant Examiner* — Gary E Hollinden
(74) *Attorney, Agent, or Firm* — Roylance, Abrams, Berdo & Goodman, L.L.P.

(57) ABSTRACT

The present invention relates to methods and apparatus for conducting an assay. In particular, the present invention relates to a rotatable platform which can be used for conducting an assay, in particular multi-step assays. The present invention provides a rotatable platform adapted to immobilize a first binding partner in one or more discrete areas on a surface of said platform, or to selectively immobilize a second binding partner in one or more discrete areas on a surface of said platform. The invention also relates to methods, apparatus, a kit and the use of the rotatable platform for conducting an assay. In particular, the invention has been developed primarily for use in sequencing nucleic acid by pyrosequencing, however the invention is not limited to this field.

19 Claims, 14 Drawing Sheets

(52) U.S. Cl.
CPC .... *B01L 3/50851* (2013.01); *B01L 2300/0864* (2013.01); *B01L 2400/0409* (2013.01); *G01N 35/00069* (2013.01); *G01N 2035/00495* (2013.01); *B01J 2219/00326* (2013.01); *B01J 2219/0049* (2013.01); *B01J 2219/00536* (2013.01); *B01J 2219/0061* (2013.01); *B01J 2219/00612* (2013.01); *B01J 2219/0063* (2013.01); *B01J 2219/00637* (2013.01); *B01J 2219/00722* (2013.01); *B01L 2300/0803* (2013.01)
USPC .......................................... 435/6.1; 435/6.11

(56) References Cited

U.S. PATENT DOCUMENTS

| | | | |
|---|---|---|---|
| 5,750,341 | A | 5/1998 | Macevicz |
| 5,922,617 | A * | 7/1999 | Wang et al. .................. 436/518 |
| 6,258,533 | B1 * | 7/2001 | Jones ............................ 435/6.18 |
| 7,033,747 | B2 * | 4/2006 | Gordon ............................... 435/4 |
| 8,080,410 | B2 * | 12/2011 | Corbett et al. ............. 435/288.4 |
| 8,440,404 | B2 * | 5/2013 | Makarov et al. ............. 435/6.11 |
| 8,481,259 | B2 * | 7/2013 | Gordon et al. ................. 435/6.1 |
| 8,574,835 | B2 * | 11/2013 | Hinz et al. ..................... 435/6.1 |
| 8,592,153 | B1 * | 11/2013 | Bustillo et al. ................. 435/6.1 |
| 2004/0234970 | A1 * | 11/2004 | Yoo ................................... 435/6 |
| 2005/0202471 | A1 * | 9/2005 | Tooke et al. ...................... 435/6 |
| 2006/0223061 | A1 | 10/2006 | Corbett et al. |
| 2008/0131904 | A1 * | 6/2008 | Parce et al. ....................... 435/6 |
| 2010/0028978 | A1 | 2/2010 | Angros |
| 2011/0009275 | A1 * | 1/2011 | Leamon et al. .................... 506/2 |
| 2011/0118139 | A1 * | 5/2011 | Mehta et al. ....................... 506/9 |
| 2011/0217697 | A1 * | 9/2011 | Rothberg et al. .............. 435/6.1 |
| 2011/0311980 | A1 * | 12/2011 | Pollack et al. ............... 435/6.12 |
| 2013/0090248 | A1 * | 4/2013 | Link et al. .......................... 506/2 |
| 2013/0164742 | A1 * | 6/2013 | Pollack et al. ............... 435/6.11 |
| 2013/0203049 | A1 | 8/2013 | Corbett et al. |
| 2013/0288254 | A1 * | 10/2013 | Pollack et al. ............... 435/6.12 |
| 2013/0323732 | A1 * | 12/2013 | Anderson et al. ............ 435/6.11 |
| 2014/0193807 | A1 * | 7/2014 | Pamula et al. ................. 435/6.1 |

FOREIGN PATENT DOCUMENTS

| | | | |
|---|---|---|---|
| WO | 93/23564 | 11/1993 | |
| WO | WO 98/49340 | * 11/1998 | ............... C12Q 1/68 |
| WO | 2005/093388 | 10/2005 | |
| WO | 2007/073107 | 6/2007 | |

OTHER PUBLICATIONS

Mashayekhi, F. et al., Analysis of read-length limiting factors in pyrosequencing chemistry, Anal Biochem, 2007, vol. 363, No. 2, pp. 275-287.

International Search Report for PCT/AU2010/000953, dated Oct. 6, 2010.

Zackrisson, A.L. et al., Identification of CYP2D6 alleles by single nucleotide polymorphism analysis using pyrosequencing, Eur. J. Clin. Pharmacol., 2003, vol. 59, pp. 521-526.

* cited by examiner

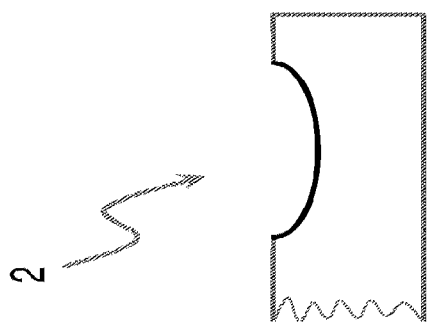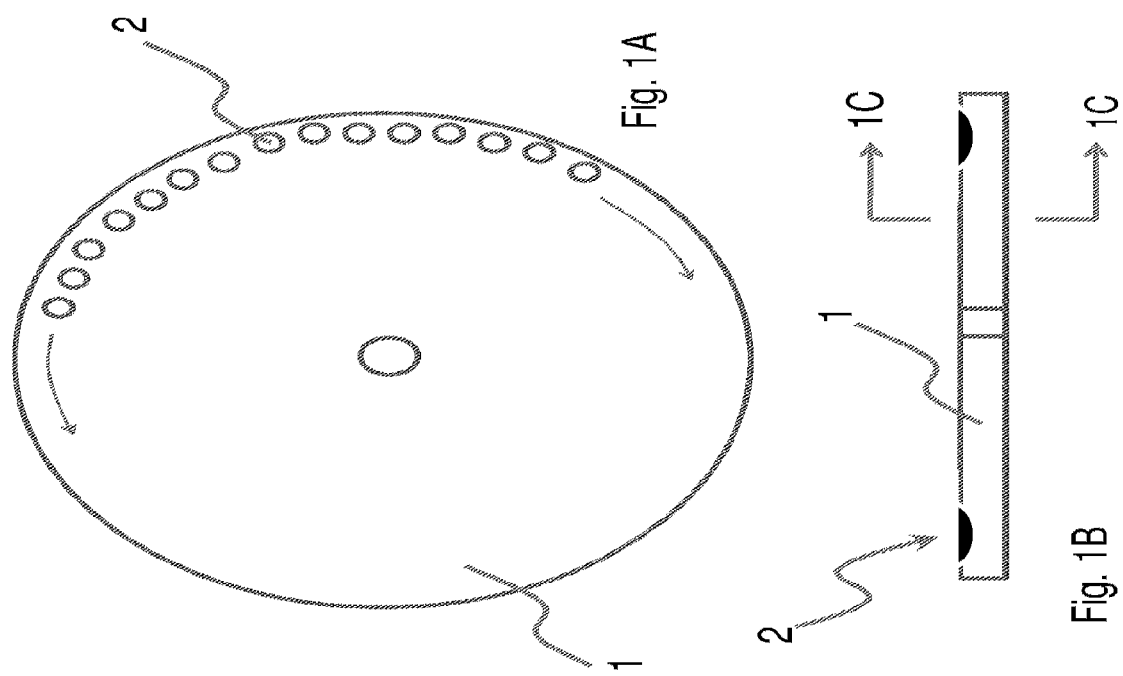

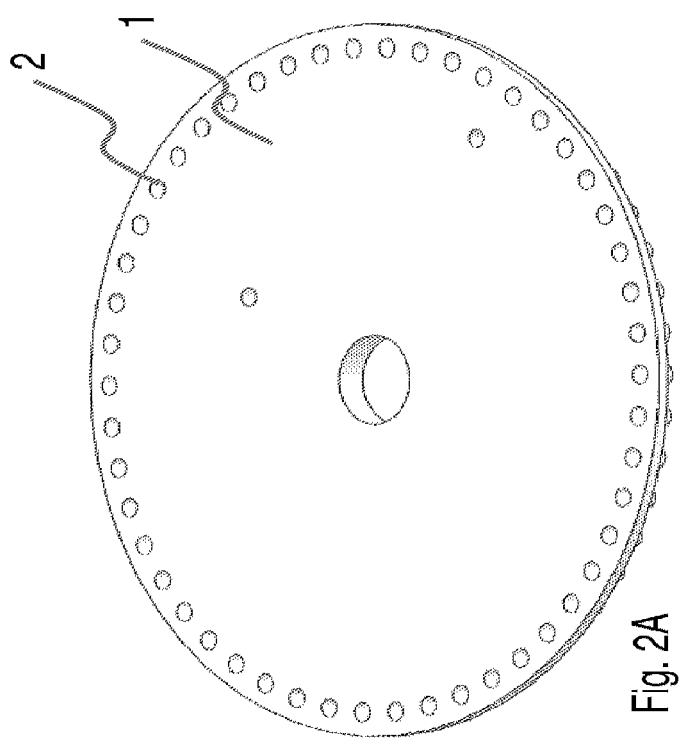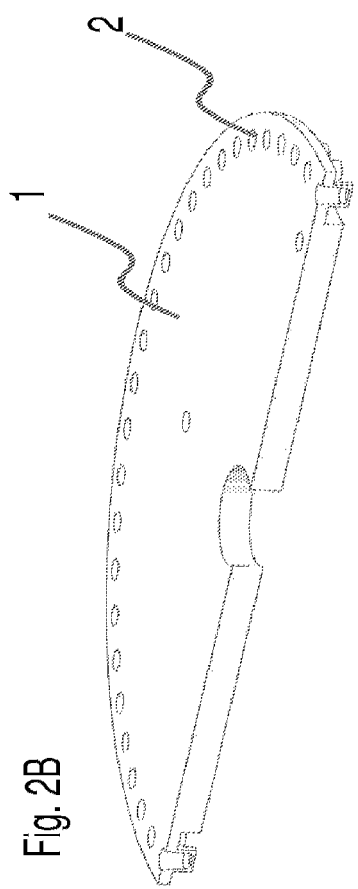
Fig. 2A
Fig. 2B

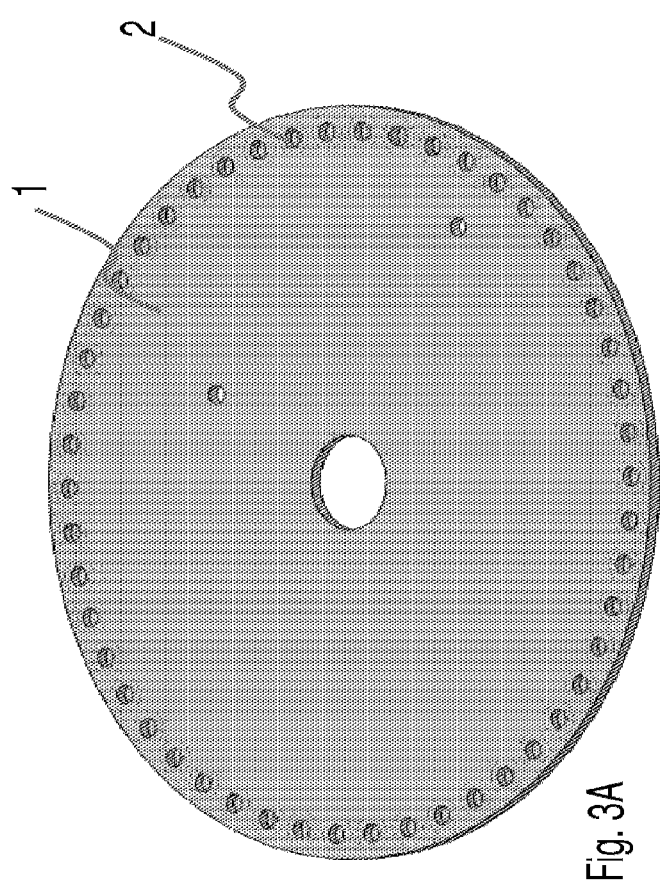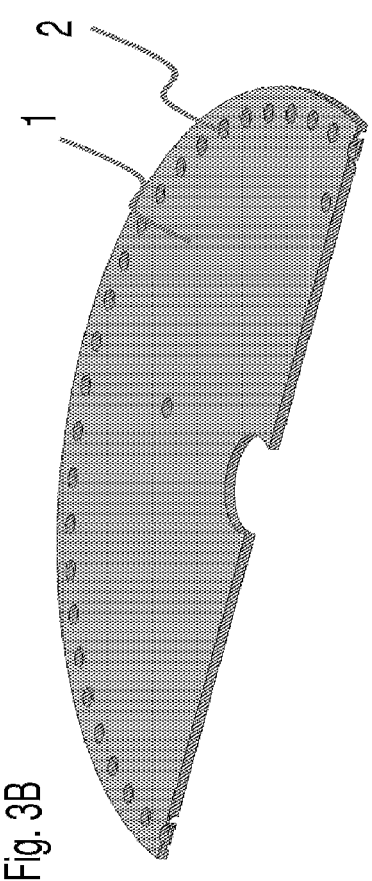
Fig. 3A
Fig. 3B

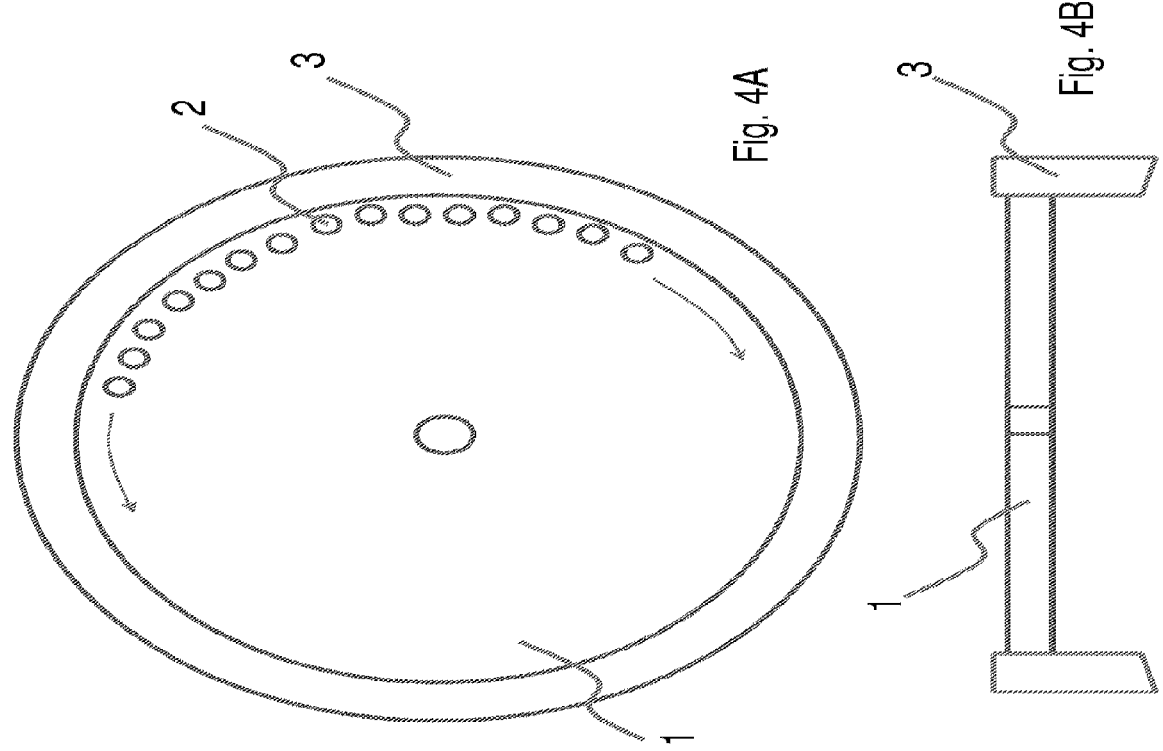

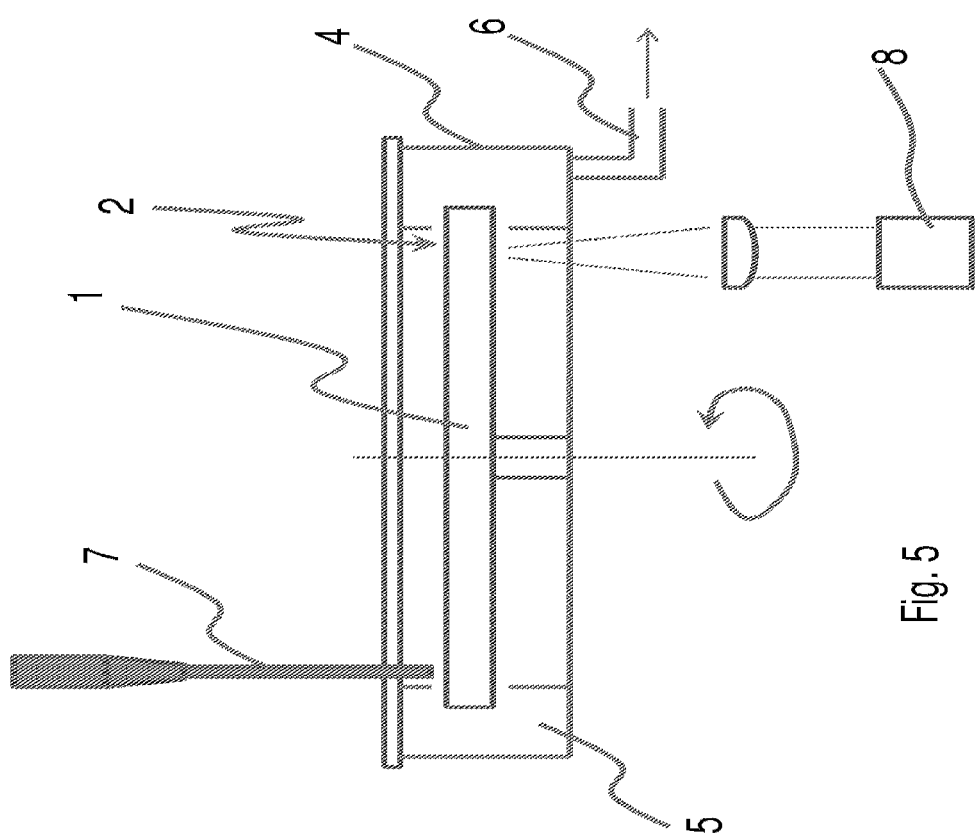

METHOD AND APPARATUS FOR CONDUCTING AN ASSAY

FIELD OF THE INVENTION

The present invention relates to a method and apparatus for conducting an assay. In particular, the present invention relates to a rotatable platform which can be used for conducting an assay, in particular multi-step assays. Whilst the invention has been developed primarily for use in sequencing nucleic acid by pyrosequencing, and will be described hereinafter with reference to this application, it will be appreciated that the invention is not limited to this particular field of use.

BACKGROUND OF THE INVENTION

The following discussion of the prior art is provided to place the invention in an appropriate technical context and enable the advantages of it to be more fully understood. It should be appreciated, however, that any discussion of the prior art throughout the specification should not be considered as an express or implied admission that such prior art is widely known or forms part of common general knowledge in the field.

The ability to determine DNA nucleotide sequences has become increasingly important in recent times. Previously, the two most commonly used methods for DNA sequencing are the enzymatic chain-termination method and the chemical cleavage technique, which both rely on gel electrophoresis to resolve, according to their size, DNA fragments produced from a larger DNA segment. The electrophoresis step and the detection of the separated DNA-fragments are cumbersome procedures. However, whilst automated electrophoresis units are commercially available, electrophoresis is not well suited for large-scale genome projects or clinical sequencing where relatively cost-effective units with high throughput are needed. Thus, the need for non-electrophoretic methods for sequencing is significant.

Techniques enabling the rapid detection of a single DNA base change are also important tools for genetic analysis. A mini-sequencing protocol based on a solid phase principle was described previously, wherein the incorporation of a radio labelled nucleotide was measured and used for analysis of the three-allelic polymorphism of the human apolipoprotein E gene. However, radioactive methods are not well suited for routine clinical applications and hence the development of a simple non-radioactive method for rapid DNA sequence analysis has also been of interest.

Methods of sequencing based on the concept of detecting inorganic pyrophosphate (PPi) which is released during a polymerase reaction have been described previously (see International PCT Publication No.'s WO 93/23564 and WO 89/09283) and commonly referred to as pyrosequencing. As each nucleotide is added to a growing nucleic acid strand during a polymerase reaction, a pyrophosphate molecule is released. It has been found that pyrophosphate released under these conditions can be detected enzymically e.g. by the generation of light in the luciferase-luciferin reaction. Such methods enable a base to be identified in a target position and DNA to be sequenced simply and rapidly whilst avoiding the need for electrophoresis and the use of harmful radiolabels.

Early prior art methods for conducting pyrosequencing employed a 0.2 mL microcentrifuge tube (or similar) with reagents being added to the tube sequentially to detect the sequence of the DNA present in the tube. Whilst this method is relatively simple, the method suffers from the drawback that the read lengths are short, since the reaction is diluted with each addition of nucleotide reagent and/or reaction by-products are accumulated and the reaction conditions reach a point where the reaction no longer proceeds. For example, typically only about 80 bases can be sequenced reliably with this method.

Commercial equipment which utilise pyrosequencing have also been developed. These systems use flow cells to perform hybridisation of a target DNA/RNA molecule. To explain, single-stranded DNA is immobilised on a stationary bead which is positioned in the flow cell, typically by immobilising a double-stranded DNA and denaturing the complementary strand. Reagents, including a nucleotide (A, G, C, or T) are flowed past the bead and light is detected if a nucleotide is incorporated. The signal strength of the light is proportional to the number of nucleotides incorporated in a single reaction. Between exposing the bead to different nucleotides a wash step is also performed and the process is repeated to detect incorporation of the next nucleotide.

Other methods of sequencing by synthesis are also known, for example by using fluorescently-labelled nucleotides. In such a method DNA samples are first fragmented and the DNA double-helix is melted into single strands. The single DNA molecules are captured on a surface within a flow cell and serve as templates for the sequencing-by-synthesis process. Fluorescently-labelled nucleotides are added one at a time and incorporated into the growing complementary strand by a DNA polymerase enzyme. Unused nucleotides are washed away. Upon illumination with a laser, the incorporated nucleotides emit light that is detected. The fluorescent label is removed before the next nucleotide is added to continue the cycle. Tracking nucleotide incorporation determines the exact sequence of each individual DNA molecule.

Sequencing by ligation is also known. This DNA sequencing method uses the enzyme DNA ligase to identify the nucleotide present at a given position in a DNA sequence. The mismatch sensitivity of a DNA ligase enzyme is used to determine the underlying sequence of the target DNA molecule. See for example U.S. Pat. Nos. 5,750,341 and 4,883,750.

What is needed is apparatus for conducting assays and analyses, which can be used with a variety of chemistries and detection methods, and in particular for conducting assays that involve multiple reaction and washing steps such as used in sequencing nucleic acid. Further, what is needed is apparatus which can be used as a convenient replacement for assays which require a flow-through environment, or to replace fixed reaction vessel assays where, in case of nucleic acid sequencing, dilution effects limit the maximum sequencing read length.

It is an object of the present invention to overcome or ameliorate at least one of the disadvantages of the abovementioned prior art, or to provide a useful alternative.

SUMMARY OF THE INVENTION

According to a first aspect the present invention provides a rotatable platform for conducting an assay, said platform adapted to immobilise a first binding partner in one or more discrete areas on a surface of said platform.

According to a second aspect the present invention provides a rotatable platform for conducting an assay, said platform adapted to selectively immobilise a second binding partner in one or more discrete areas on a surface of said platform.

In one embodiment the entire upper surface of the platform is adapted to immobilise a first binding partner or selectively immobilise a second binding partner. However, in other embodiments a plurality of discrete areas or predefined sites or target sites are provided on the surface of the platform, or alternatively a secondary surface which is relatively easily bound to the surface of the platform (e.g. beads) to immobilise a first binding partner or selectively immobilise a second binding partner. In another example, the discrete areas are a coating on the rotatable platform, wherein the coating is adapted to immobilise the first binding partner.

In some embodiments, the first binding partner is chemically adsorbed on the surface of the platform. In other embodiments, the first binding partner is covalently or ionically or hydrogen bonded to the surface of the platform, and in yet other embodiments van der Waals forces hold the first binding partner to the surface of the platform. It will be appreciated that the second binding partner is bindable or reactable to the first binding partner already bound to the surface of the platform.

The present invention is particularly relevant to methods and assays such as nucleic acid sequencing methods, for example pyrosequencing. For example, the first and second binding partners are binding partner pairs (optionally one of which may be detectably labelled), which are preferably selected from avidin or streptavidin or streptactin or analogs and biotin or analogs. However, and as discussed further below, an advantage of the present invention is to provide relatively fast and relatively simple washing steps, and associated low waste volumes of washing solution and reagents.

The present invention will now be explained in the context of pyrosequencing, however it will be appreciated that the invention is not limited to this assay.

It will be appreciated that in the first aspect the platform adapted to immobilise a first binding partner, which may be for example avidin or streptavidin or streptactin or analogs, and then the avidin or streptavidin or streptactin or analogs can be subsequently reacted with say, biotinylated DNAs, in a subsequent processing step. It will be further appreciated that in the second aspect the platform already comprises a first binding partner, and the platform is adapted to selectively immobilise a second binding partner. It will therefore be appreciated that the platform according to the first aspect can be considered to be 'unfunctionalised', and the platform according to the second aspect can be considered to be 'functionalised' or 'pre-functionalised'.

According to a third aspect the present invention provides a method for conducting an assay, said method comprising the steps of:
    providing a platform according to the first aspect;
    binding or immobilising a first binding partner to one or more discrete areas on said surface of said platform or surfaces embedded in the surface of said platform (e.g. beads); and
    contacting sequentially each said discrete area with a series of reagents, wherein between one or more or all of said contacting steps said platform is rotated such that any residual or unreacted said reagent is substantially centrifugally removed from each said discrete area.

Preferably the first of the series of reagents comprises the second or complementary binding partner to the first binding partner, and then the subsequent reagents are chosen from, say, washing or rinsing reagents, and as discussed further below.

According to a fourth aspect the present invention provides a method for conducting an assay, said method comprising the steps of:
    providing a platform according to the second aspect;
    selectively binding or immobilising a second binding partner to one or more discrete areas on said surface of said platform or surfaces embedded in the platform; and
    contacting sequentially each said target site with a series of reagents, wherein between one or more or all of said contacting steps said platform is rotated such that any residual or unreacted said reagent is substantially centrifugally removed from said target site.

Preferably the method of the invention further comprises the step of analysing the assay during and/or after each said contacting step. In preferred embodiments, prior to contacting the discrete areas with a subsequent reagent each said discrete area is subjected to a washing or rinsing step with a washing reagent. The washing reagent may be any reagent which can substantially wash off any residual solution from the previous contacting step or reduce the amount of any residual solution and the components present in said solution (active agents like, e.g., apyrase or other suitable enzymes which degrade by-products or otherwise reduce the concentration of by-products).

Whilst the washing reagent may be any reagent which can substantially wash off any residual solution from the previous contacting step or reduce the amount of any residual solution and the components present in said solution, and may be an active agent like apyrase, in other embodiments preferably the washing step for removal of excess nucleotide is free from apyrase, as detailed in Mashayekhi F., and Ronaghi M., *Analysis of read-length limiting factors in pyrosequencing chemistry, Anal. Biochem.* (2007), 363(2): 275-287, which is incorporated in its entirely herein by reference. As detailed in Mashayekhi et al, replacing the washing step with an apyrase-free washing step her been shown to improving the read-length of pyrosequencing.

Preferably the rotatable platform is rotated at low speed whilst dispensing the reagents, for example at between about 10 to 200 rpm, so as not to remove reagents added to the target site; and the platform is rotated at high speed whilst dispensing the reagents, for example at between about 400 to 1000 rpm. However, it will be appreciated that other rotational speeds are possible.

In preferred embodiments, each said discrete area is prepared for each said subsequent reagent by substantially 'drying' said discrete area by rotation of said platform to centrifugally remove any residual reagents such that there is a substantially reduced, preferably substantially no, contamination of said discrete area with the reagent from the previous step.

According to a fifth aspect the present invention provides use of the platform according to the first or second aspects for conducting an assay.

According to a sixth aspect the present invention provides a kit comprising the platform according to the first or second aspects and one or more reagents for said assay.

According to a seventh aspect the present invention provides apparatus for conducting an assay, said apparatus comprising:
    apparatus for rotating said platform according to said first or second aspects at a predetermined controllable user-selectable rotational speed;
    optionally apparatus for dispensing said first binding partner onto said one or more discrete areas on said surface of said platform for immobilising said first binding partner to said discrete areas, or apparatus for dispensing said second binding partner onto said one or more discrete areas on said surface of said platform for selectively immobilising said second binding partner to said discrete areas;
apparatus for dispensing reagents into contact with said discrete areas; and optionally apparatus for dispensing a washing reagent.

Preferably the apparatus for rotating the platform is a motor, and the predetermined rotational speeds are user-selectable and between about 10 to 1000 rpm. The apparatus is also preferably provided with a vacuum extraction system to extract the waste reagents which are spun off the rotatable platform.

In an alternative design, the rotatable platform does not necessarily need to be a disc per se; it could be comprised of a plurality of discrete reaction wells which are loaded into a cradle for holding each discrete reaction well in a rotary format. For example a modified 0.2 mL microfuge tube can be mounted at 45 degrees on a platform in the form of a rotatable cradle. In this configuration the cap of the microfuge tube is open and is positioned on the horizontal plane (the inside surface of the cap facing upward). The cap is modified such that reagents dispensed into/onto the cap at low rpm could be spun into the tube at high rpm. The plastic hinge of the microfuge tube is also preferably modified to act as a channel to direct waste reagent from the cap to the tube. The cap serves as the discrete area to receive and immobilise a first binding partner, or receive and selectively immobilise a second binding partner, and then receive subsequent reagents, and the tube itself would serve as the waste trough/container. The advantage is the operator could load one sample or many by inserting the desired number of tubes into the cradle.

According to an eighth aspect the present invention provides apparatus for conducting an assay, said apparatus comprising:
a plate comprising a discrete area adapted to immobilise a first binding partner or adapted to selectively immobilise a second binding partner; and
a container connected to said plate by a flange, wherein said flange comprises a channel for the passage of fluid from said plate to said container.

Preferably the container comprises an open top and the plate comprises a flange adapted to selectively engage the open top of the container and provide a fluid tight seal therewith. Preferably the plate is a cap for the container.

Preferably the container comprises a radially outwardly extending annular flange for supporting the container in a holder, such as a carousel. Preferably the container is substantially cylindrical. Preferably said container is disposable, and made of plastics materials.

Preferably the apparatus for conducting an assay according to the seventh aspect is a modified microfuge/microcentrifuge tube, such as a modified Eppendorf®.

According to a ninth aspect the present invention provides a rotatable cradle, said cradle being adapted to receive 2 or more plates, each plate comprising a discrete area adapted to immobilise a first binding partner or adapted to selectively immobilise a second binding partner. Preferably the rotatable cradle is also adapted to receive 2 or more containers, each container connected to a respective plate by a flange, wherein said flange comprises a channel for the passage of fluid from said plate to said container. Preferably said plate is the cap of a modified microcentrifuge tube and said container is the microcentrifuge tube itself. Preferably the ninth aspect utilises the apparatus according to the eighth aspect.

According to a tenth aspect the present invention provides a method for conducting an assay, said method comprising the steps of:
providing a rotatable cradle according to the ninth aspect and apparatus according to the eighth aspect;
engaging at least one plate to said platform;
binding or immobilising a first binding partner to said discrete area, or selectively binding or immobilising a second binding partner to said discrete area; and
contacting sequentially each said discrete area with a series of reagents, wherein between each or any of said contacting steps said rotatable cradle is rotated such that any residual or unreacted said reagent is substantially centrifugally removed from said discrete area.

According to an eleventh aspect the present invention provides use of the rotatable cradle according to the ninth aspect for conducting an assay, or use of the apparatus according to the eighth aspect for conducting an assay.

According to a twelfth aspect the present invention provides a kit comprising the apparatus according to the eighth aspect and one or more reagents for said assay.

According to a thirteenth aspect the present invention provides a kit comprising the rotatable cradle according to the ninth aspect and one or more reagents for said assay.

According to a fourteenth aspect the present invention provides apparatus for conducting an assay, said apparatus comprising:
apparatus for rotating said rotatable cradle according to the ninth aspect at a predetermined controllable user-selectable rotational speed;
optionally apparatus for dispensing a first binding partner or a second binding partner onto said discrete area; and
apparatus for dispensing one or more reagents into contact with said discrete area(s).

Other aspects of the present invention relate to conducting an assay in parallel. For example, according to a fifteenth aspect the present invention provides a rotatable cylinder for conducting assays, said cylinder having at least one circumferentially extending lane, each said lane comprising one or more discrete areas adapted to immobilise a first binding partner or adapted to selectively immobilise a second binding partner. It will be appreciated that in this aspect the present invention provides a cylinder for conducting an assay, wherein said cylinder is adapted or configured to be rotatable. The skilled person will appreciate that this embodiment enables many samples to be run simultaneously or in parallel.

It will be appreciated that the rotatable cylinder may be housed in a container having a longitudinally extending aperture to enable the binding partner and reagents, etc to be dispensed onto the discrete areas. Of course it will be appreciated that detection elements will be in the tangential path of the waste fluids when the cylinder is rotated at high speed. Therefore, this may be avoided by using a shutter for closing the longitudinally extending aperture during centrifugation.

According to a sixteenth aspect the present invention provides a method for conducting an assay, said method comprising the steps of:
providing a rotatable cylinder according to the fifteenth aspect;
binding or immobilising said first binding partner to one or more discrete areas, or selectively binding or immobilising a second binding partner to one or more discrete areas; and
contacting sequentially each said discrete area with a series of reagents, wherein between each or any of said contacting steps said rotatable cylinder is rotated such that any residual or unreacted said reagent is substantially centrifugally removed from said discrete areas.

According to a seventeenth aspect the present invention provides use of the rotatable cylinder according to the fifteenth aspect for said assay.

According to an eighteenth aspect the present invention provides a kit comprising the rotatable cylinder according to the fifteenth aspect and one or more reagents for said assay.

According to a nineteenth aspect the present invention provides apparatus for conducting an assay, said apparatus comprising:

apparatus for rotating said rotatable cylinder according to said fifteenth aspect at a predetermined controllable user-selectable rotational speed;

optionally apparatus for dispensing said first or second binding partner onto one or more discrete areas for immobilising or selectively immobilising respectively said binding partner to said discrete areas; and apparatus for dispensing reagents into contact with said discrete areas.

The present invention will now be explained in the context of pyrosequencing, however it will be appreciated that the invention is not limited to this assay.

Pyrosequencing

In a twentieth aspect, the assay is pyrosequencing, and the present invention provides a rotatable platform for conducting sequencing of a nucleic acid strand, said platform adapted to immobilise a nucleic acid strand binding partner in one or more discrete areas on a surface of said platform or on beads embedded in said surface.

In a twenty-first aspect, the assay is pyrosequencing, and the present invention provides a rotatable platform for conducting sequencing of a nucleic acid strand, said platform adapted to selectively immobilise a nucleic acid strand in one or more discrete areas on a surface of said platform or on beads embedded in said surface.

Preferably the sequencing method employed is pyrosequencing. However, it will be appreciated that other methods of sequencing a nucleic acid strand may be utilised, as discussed further below.

Preferably said nucleic acid strand is DNA or RNA or a modified form(s) thereof e.g following bisulfite treatment or covering additional bases which are not present in naturally occurring nucleic acids. It will be appreciated that copies of the nucleic acid strand are retained on each of the one or more discrete areas.

Preferably the rotatable platform is substantially circular and has a diameter between about 50 to 500 mm Preferably the rotatable platform comprises between about 2 to 500 discrete areas which are equidistantly spaced from the centre of the rotatable platform. It will be appreciated that the diameter may be any diameter, and the diameter may be chosen to accommodate the number of discrete areas, which may be 2 or more in number. In preferred embodiments the discrete areas are distributed or positioned substantially evenly around the periphery of the rotatable platform to form a substantially circular array.

Preferably the discrete areas are adapted to selectively bind, capture, or immobilise a nucleic acid strand (e.g. the sequencing template or the sequencing primer). For example in some preferred embodiments the nucleic acid strand is biotinylated and the discrete areas comprise avidin, and preferably streptavidin or an analogue, for binding the biotinylated nucleic acid strand. Alternatively, the discrete areas or the beads are adapted to bind, capture, or immobilise avidin, and preferably streptavidin, and in a subsequent step the biotinylated nucleic acid strand is selectively immobilised to the avidin/streptavidin bound to the discrete areas. However, it will be appreciated that other chemistries are available for immobilising a nucleic acid strand to a discrete areas. The present invention is not limited to the chemistry which can be employed to immobilise the nucleic acid strand to the discrete areas.

It will be appreciated by the skilled person that the discrete areas on the rotatable platform may also require a treatment in order to allow the streptavidin (or an equivalent chemistry, as discussed above) to selectively bind or adhere thereto. For example, if the material which the rotatable platform is formed from is polycarbonate then streptavidin resists binding to or does not bind to this polymer. Therefore, the discrete areas may require a coating of a material which streptavidin binds to, such as polystyrene. Of course it will be appreciated by the skilled person that materials other than polystyrene can be used to create the discrete areas for the streptavidin to bind to, and therefore eventually enable the biotinylated nucleic acid strand to be immobilised to the discrete areas. Preferably the discrete areas comprise a treatment adapted to enable the nucleic acid to be selectively immobilised thereto.

In one embodiment the platform of the invention is a disposable item, however in alternative embodiments the platform is suitable to be 'cleaned' of, say, nucleic acid and reused in a further assay. For example the platform may be formed of a ceramic or glass.

In one embodiment the discrete areas are simply zones or regions on the surface of the rotatable platform which are adapted to receive and selectively retain the nucleic acid strand, or the avidin/streptavidin. The discrete areas may be substantially flat, or have the same topography as the rotatable platform. In other preferred embodiments, however, the discrete areas may be shallow wells, which may comprise a volume of between about 0.5 to 100 µL. It will be appreciated that the shallow wells may be any shape, and that the wells may be any volume. However, in view of the relatively small amount of reagents being utilised in typical pyrosequencing analyses/assays the wells are adapted to contain only a low volume, such as between about 0.5 to 10 µL. In other embodiments it is contemplated that the discrete areas could even be relatively raised portions compared to the surface of the rotatable platform.

In preferred embodiments the discrete areas are about 1 to 5 mm in diameter. However, it will be appreciated that the discrete areas could be any diameter or shape when viewed in plan view.

Preferably the rotatable platform is conveniently formed of a plastics material, however, it will be appreciated by the skilled person that other materials are possible, such as glass or quartz. Preferably the plastics material is selected from the group consisting of polycarbonate, polystyrene, or polypropylene. It is also contemplated that the rotatable platform could also be a laminated structure. Whatever the material which the rotatable platform is formed from the platform must be capable of withstanding rotation without deformation, and potentially withstand thermal effects for denaturing the nucleic acid, as discussed further below.

In some preferred embodiments the rotatable platform, which may be a substantially circular disc, further comprises a trough disposed at the periphery of the platform for receiving waste fluids which are spun off or centrifuged away from the surface of the rotatable platform during its rotation. It will be appreciated that once each step or number of steps of the pyrosequencing reaction is completed the unused or waste reagent in contact with the discrete areas should be removed to achieve long read lengths. Creation of centrifugal force by rotation of the rotatable platform causes the waste fluids to be spun off the platform, and in order to improve the handling of the waste fluids a trough is provided.

Alternatively wastes reagents could be spun off the platform every 50 cycles of nucleotide addition, or just before the reagents become sufficiently diluted so as to inhibit the reaction.

In this embodiment it will be appreciated that the total mass of the rotatable platform will increase as additional pyrosequencing reagents are added to the discrete areas and then spun off the platform after each pyrosequencing reaction is complete. Therefore, in an alternative embodiment, it may be desirable that the rotatable platform not include a trough and the housing within which the rotatable platform is positioned be configured to have a trough disposed adjacent the periphery of the platform, such that waste fluids which are spun off the surface of the rotatable platform during its rotation are caught in this 'stationary' trough.

The skilled person, familiar with the techniques and chemistry behind pyrosequencing, will appreciate that the nucleic acid strand immobilised to the discrete areas may need to be denatured to remove the complementary nucleic acid strand. Denaturing may be achieved by any method, however preferred examples comprise heating the discrete areas or even the entire rotatable platform to a temperature sufficient to denature, e.g. 94 to 99° C., or by exposing the discrete areas to a solvent heated to in excess of 94° C., such as a buffer. Alternatively, the discrete areas may be exposed to a denaturing composition (e.g. compositions comprising NaOH). Other methods include heating by infra-red or equivalent radiation. It will be appreciated that the rotatable platform should be formed of materials which are capable of withstanding such denaturing conditions.

The rotatable platform could also be enabled to heat and cool so as to hybridise or melt DNA to the captured nucleic acid target or to the captured sequencing primer. In the case of pyrosequencing, once the dsDNA target has been captured and denatured, a sequencing primer is added to hybridise to the ssDNA or, alternatively, the ssDNA is hybridized to the captured sequencing primer. In this case the rotatable platform may be heated to remove any tertiary structures in the ssDNA and then cooled to hybridise the sequencing primer to the immobilised target.

It will be appreciated that heating the chamber may add somewhat to the complexity of the device, since when relatively small volumes of reagents are used the chamber is sealed by suitable means. Alternatively, one may use an oil overlay to reduce evaporation during the heating phase. Other suitable means are well known to the artisan. Alternatively, denaturation reagent could be added to the captured ssDNA and sequencing primer, then buffer of a lower pH added to reduce the pH over the target site and anneal the sequencing primer to the DNA target. Once annealed, the pH buffer may be spun off to waste.

The skilled person will appreciate the many advantages which the present invention, in various embodiments, is capable of providing. For example, the present invention enables an increased base read length compared to prior art devices and methods. To explain, prior art methods conduct pyrosequencing in a 0.2 mL microcentrifuge tube (or similar) and reagents are added to the tube sequentially to detect the sequence of the DNA present in the tube. The nucleotides are added sequentially to the reaction containing the DNA in reaction buffer, all enzymes and the substrate(s). The reaction is performed in a 96 or 24 well plate. The plates are heated (28° C.) and shaken during the reaction. Hence, the volume of nucleotides added is more or less equivalent to the volume which evaporates which does not result in a dilution of the reaction mixture but in an accumulation of byproducts. The prior art methods suffer from the drawback that the read lengths are comparatively short which is most likely based on the accumulation of degradation products, e.g. generated by the activity of the apyrase. The present invention does not offer the drawbacks known from the state of the art, since the immobilised nucleic acid strand is contacted with a nucleotide, the remaining nucleotides as well as all reaction products and by-products are subsequently substantially removed from the discrete area as described above, the discrete area is also optionally washed before being contacted with a subsequent nucleotide reagent. It is contemplated that base read length of in excess of 300 or 400 bases are possible, and with improvements to chemistry potentially in excess of 1000 bases.

Further advantages will be evident to the skilled person, however for clarity the invention provides relatively simpler apparatus than prior art flow-through cells. Even further advantages relate to potentially relatively faster sequencing than prior art methods and devices, and that potentially lower volumes of reagents required compared to the prior art. A further limitation of prior art methods, and in particular the method of conducting Pyrosequencing, is the very long time needed for one reaction cycle, i.e. the addition of one nucleotide. The time needed for one reaction cycle is normally about 60 seconds or even more which is based on the time needed to degrade all the remaining nucleotides of the previous reaction cycle. Only after complete degradation of substantially all remaining nucleotides of the previous reaction cycle the next nucleotide is added. It will be appreciated that the apparatus as herein described enables the remaining nucleotides to be removed at a much higher speed (i.e. via centrifugation steps, washing steps). This results in a much shorter cycle time for one base being incorporated, most likely approximately 15 seconds, thereby creating an approximate at least a four-fold decrease in run time.

The present invention also enables improved fluid handling compared to some prior art devices. It is also possible that the present invention could provide increased sensitivity compared to prior art devices given a high-speed photomultiplier can be used instead of a CCD array.

Pyrosequencing is a method of DNA sequencing based on the 'sequencing by synthesis' principle, which relies on detection of pyrophosphate release on nucleotide incorporation rather than chain termination with dideoxynucleotides. 'Sequencing by synthesis' involves taking a single strand of DNA to be sequenced and then synthesizing its complementary strand enzymatically. The 'sequencing by synthesis' methods are based on detecting the activity of a DNA polymerase (a DNA synthesizing enzyme) by detecting a reaction byproduct of the nucleotide addition reaction of the DNA polymerase (DNA+xdNTP->DNA$_{+1}$+PPi or a different byproduct depending on x. x can also be ATP). In the Pyrosequencing reaction the PPi is quantified using an enzyme cascade which generates light.

1. Sulfurylase: APS+PPi→ATP+SO$_4$
2. Luciferase: Luciferin+ATP→Oxoluciferin+PPi+Light
3. Apyrase: degradation of remaining dNTPs and ATP Furthermore, there are several reactions known in the art which may be used to quantify the byproducts like e.g. the use of PPDK (phosphoenol pyruvate dikinase) which transform PPi+PEP+AMP->Pyruvate+ATP+Pi. Furthermore the byproducts may be detected by e.g. change in pH or other detectable parameter changes. The 'sequencing by synthesis' methods may alternatively be based on detecting the activity of a DNA ligase detecting a reaction by-product of the primer addition reaction of the DNA ligase. Suitable methods are well known to a person skilled in the art.

Essentially, the method allows sequencing of a single strand of DNA by synthesizing the complementary strand along it, one base pair at a time, and detecting which base was actually added at each step. The template DNA or the sequencing primer is immobilized, and solutions of A, C, G, and/or T nucleotides are added and removed after the reaction, sequentially. Light is produced only when the added nucleotide complements the first unpaired base or bases of the template. The sequence of added nucleotides which produce detectable signals, e.g. chemiluminescent signals, allows the determination of the sequence of the template. ssDNA template is hybridized to a sequencing primer or vice-versa and incubated with the enzymes DNA polymerase, and optionally ATP sulfurylase, luciferase and/or apyrase, and—by way of example—with the substrates adenosine 5'phosphosulfate (APS) and luciferin. Other reaction cascades providing a detectable signal are well known to the artisan.

In broad overview, pyrosequencing follows the following general steps:
1. The addition of one of the four deoxynucleotide triphosphates (dNTPs) or suitable derivatives thereof to the nucleic acid strand template. The DNA polymerase incorporates the correct, complementary dNTP or its derivative onto the template, which releases pyrophosphate (PPi) stoichiometrically.
2. ATP sulfurylase quantitatively converts PPi to ATP. This ATP triggers the luciferase-mediated conversion of luciferin to oxyluciferin that generates visible light in amounts that are proportional to the amount of ATP. The light produced in the luciferase-catalyzed reaction is detected and analyzed.
3. Unincorporated nucleotides and ATP are subsequently degraded by apyrase or other suitable enzymes.

Several modifications to the classic pyrosequencing protocol are well known in the art and are well suited to be performed on an apparatus according to the present invention. Since the light produced in every single nucleotide incorporation step is proportional to the amount of nucleotides incorporated, suitable software allows for transformation the generated light information in a specific nucleotide sequence pattern. In classic Pyrosequencing, the light pattern is called 'pyrogram'. Furthermore, said software preferably allows for the quantification of incorporation ratios of mixed populations at specific positions.

The present invention contemplates sequencing methods that comprise the steps of immobilising the nucleic acid template to be sequenced or the sequencing primer and cycles of step-wise nucleotide additions. Whilst the present invention has been exemplified with respect to pyrosequencing, it will be appreciated that the present invention is also useful for other nucleic acid sequencing chemistries, and in particular such chemistries that benefit from a flow through environment and a solid phase. The present invention can also avoid certain of the steps referred to above, or at least make them more convenient. Pyrosequencing requires that ssDNA template is present. Optionally, the rotatable platform also serves to capture dsDNA and denature said dsDNA to leave ssDNA, for example with an annealed sequencing primer ready for pyrosequencing, thus eliminating the need for a separate isolation step. In one embodiment of the present invention, the rotatable platform may be used to generate the ssDNA by, e.g., the addition of an enzyme or enzyme mixture which effects the degradation of preferentially one of the dsDNA strands.

Specifically, the person skilled in the art would understand that the term "flowthrough DNA sequencing" includes, for example, a method of immobilizing a nucleic acid template or a sequencing primer, hybridising the primer to the template or vice-versa and perform a primer mediated synthesis in a step-wise manner in the presence of nucleotides wherein the nucleotides include, for example, optionally with a strand extension termination moiety, such as a dideoxy moiety, and optionally a detectable label (e.g. Sanger sequencing). A further nucleic acid sequencing method embodiment comprises the steps of: incorporating a labelled nucleotide into the extending primer strand; identifying the incorporated nucleotide; and removal of the strand extension termination moiety and label so that the extending strand is ready for incorporation of a successive nucleotide.

The person skilled in the art would also understand that the term "flowthrough DNA sequencing" includes, for example, nucleic acid sequencing by ligation. It would be clear that the term "nucleic acid sequencing by ligation" comprises immobilising a nucleic acid template or a sequencing primer, hybridising the primer to the template or vice-versa, followed by successive rounds of DNA ligation of, for example, labelled nucleotides or short labelled probes.

It would also be clear to the person skilled in the art that the present invention contemplates any DNA sequencing method which comprises steps of nucleic acid immobilisation and stepwise nucleotide addition and detection.

The person skilled in the art would also understand that the term "flowthrough DNA sequencing" includes all of the above mentioned techniques. also In a further embodiment the "flowthrough DNA sequencing" methods as described herein may include the use of enzyme(s) immobilized on the surface of the platform and/or on a further surface bound to or immobilized on the surface of the platform, e.g. on beads which are modified in a way that the can bind said enzyme(s).

According to a twenty-second aspect the present invention provides a method for conducting sequencing of a nucleic acid strand, said method comprising the steps of:
  providing a platform according to the twentieth aspect;
  binding or immobilising a nucleic acid strand binding partner to said discrete area and then selectively binding or immobilising a nucleic acid strand to said discrete area;
  optionally denaturing and removing any complementary nucleic acid strand, annealing a sequencing primer to the discrete area; and
  contacting sequentially each said discrete area with a series of reagents comprising A, T, G and/or C nucleotides or the respective suitable nucleotide analogs, wherein between each or any of said contacting step said platform is rotated such that substantially any residual or unreacted reagent is substantially centrifugally removed from said discrete area.

An optional washing step or enzymatic treatment may improve the removing of the residual or unreacted reagent.

According to a twenty-third aspect the present invention provides a method for conducting sequencing of a nucleic acid strand, said method comprising the steps of:
  providing a platform according to the twenty-first aspect;
  selectively binding or immobilising a nucleic acid strand to said discrete area;
  optionally denaturing and removing any complementary nucleic acid strand, annealing a sequencing primer to the discrete area; and
  contacting sequentially each said discrete area with a series of reagents comprising A, T, G and/or C nucleotides or the respective suitable nucleotide analogs, wherein between each or any of said contacting step said platform is rotated such that any residual or unreacted said reagent is substantially centrifugally removed from said discrete area.

In this aspect, it will be appreciated that the discrete area already has immobilised thereto a nucleic acid strand binding partner, and it is to this nucleic acid strand binding partner that the nucleic acid strand selectively binds.

An optional washing step or enzymatic treatment may improve the removing of the residual or unreacted reagent.

In one embodiment the sequential contacting step comprises either:
a.) A followed by T followed by G and then followed by C nucleotides, followed by A again, etc; or
b.) A+T+G+C nucleotides are added as a mixture, and the mixture added again, etc.

In another embodiment each said discrete area is contacted sequentially with a series of reagents comprising A, T, G and/or C nucleotides. The sequential contacting step may comprise one of the following:
a.) each nucleotide or its analog is added separately and sequentially in any desired or predetermined order,
b.) A+T+G+C nucleotides or any predetermined or desired subset of these are added as a mixture, and the mixture added again, etc.

The sequential contacting step a.) is particularly useful for the pyrosequencing methodology, and the sequential contacting step b.) is particularly useful if labelled nucleotides are utilised, such as fluorescently labelled nucleotides where each is labelled with a different dye.

It will be appreciated that the entire method is iterative in that the sequence of nucleotides may be added in any predefined order and/or any predefined combination and the sequence repeated a sufficient number of times as required to sequence the nucleic acid template. For example, A, T, G, and C may be added only at a known mutation site. The advantage of this embodiment it that this procedure speeds up known mutation detection, as fewer base additions are required.

Preferably the method of the invention further comprises the step of analysing the nucleic acid strand during and/or after each said contacting step. The analysis can be any analysis however it will be appreciated that in the context of pyrosequencing the analysis step comprises in each step of said analysis identifying the next base pair in the nucleic acid strand by correlating the output of light with the number of nucleotides which have been incorporated to the nucleic acid strand. All appropriate and suitable technical measures to detect the incorporation of a nucleotide may be taken by the artisan. For example, a suitable detector for detecting the light produced by the reaction is a photomultiplier. It will be appreciated that as the rotatable platform is rotated the samples pass the detector, preferably all the samples pass the detector.

In preferred embodiments, prior to contacting the discrete areas with a subsequent reagent each said discrete area is subjected to a washing or rinsing step with a washing reagent. The washing reagent may be any reagent which is suitable to wash off residual solution from the previous contacting step, preferably to wash off substantially all residual solution from the previous contacting step. However, in a preferred embodiments the washing reagent is the buffer in which the following reaction step is performed. The washing reagent may also contain washing enhancers, such as—by way of example—apyrase, phosphatase, etc. Suitable washing reagent are well known to the killed artisan.

Preferably the rotatable platform is rotated at low speed whilst dispensing the reagents and said enzyme, for example at between about 10 to 200 rpm, so as not to remove reagents added to the discrete area; and the platform is rotated at high speed whilst dispensing the washing reagent, for example at between about 400 to 1000 rpm. However, it will be appreciated that other rotational speeds are possible.

As discussed above the denaturing step may comprise heating the nucleic acid strand to effect denaturing, or exposing the nucleic acid strand to elevated pH, or exposing the nucleic acid strand to a suitable enzyme or enzyme mixture.

In preferred embodiments the method of the invention comprises the step of wherein after the nucleic acid strand is denatured the complementary strand is removed by a rinsed step with a rinsing reagent.

Preferably each said discrete areas is prepared for each said subsequent reagent by substantially drying said discrete areas by rotation of said platform to centrifugally remove any residual reagents such that there is substantially reduced contamination of said discrete area with a reagent, preferably substantially no contamination of said discrete area with a reagent.

According to a twenty-fourth aspect the present invention provides use of the platform according to the twentieth or twenty-first aspects for sequencing a nucleic acid strand.

According to a twenty-fifth aspect the present invention provides a kit comprising the platform according to the twentieth or twenty-first aspects and one or more reagents for sequencing a nucleic acid strand.

According to a twenty-sixth aspect the present invention provides apparatus for sequencing a nucleic acid strand, said apparatus comprising:
apparatus for rotating said platform according to the twentieth aspect at a predetermined controllable user-selectable rotational speed;
optionally an apparatus for dispensing a nucleic acid strand binding partner onto said discrete areas for immobilising said nucleic acid strand binding partner to said discrete areas;
optionally an apparatus for dispensing a nucleic acid strand onto said discrete areas for selectively immobilising said nucleic acid strand to said discrete areas;
optionally an apparatus for denaturing and optionally removing any complementary nucleic acid strand;
apparatus for dispensing A, T, G and/or C nucleotides or their respective analogs or combinations thereof into contact with said discrete areas;
apparatus for dispensing a washing reagent; and
optionally an apparatus for dispensing one or more enzyme solutions.

According to a twenty-seventh aspect the present invention provides apparatus for sequencing a nucleic acid strand, said apparatus comprising:
apparatus for rotating said platform according to the twenty-first aspect at a predetermined controllable user-selectable rotational speed;
optionally an apparatus for dispensing a nucleic acid strand onto said discrete area for selectively immobilising said nucleic acid strand to said discrete areas;
optionally an apparatus for denaturing and optionally removing any complementary nucleic acid strand;
apparatus for dispensing A, T, G and/or C nucleotides or their respective analogs or combinations thereof into contact with said discrete area;
apparatus for dispensing a washing reagent; and
optionally an apparatus for dispensing one or more enzyme solutions.

Preferably the apparatus for rotating the platform is a motor, and the predetermined rotational speeds are user-selectable and between about 10 to 1000 rpm. The apparatus for dispensing said nucleic acid strand, for dispensing A, T, G and/or C nucleotides, and for dispensing washing reagent can be any apparatus, however preferably the apparatus is similar to ink jet-type technology, piezo actuated or driven by air pulses. The apparatus is also preferably provided with a vacuum extraction system to extract the waste reagents which are spun off the rotatable platform. The apparatus is also provided with a suitable detection means/apparatus to detect light produced by the pyrosequencing reaction. Suitable detectors will be known to the skilled person, for example a photomultiplier which may be mounted beneath or above the rotatable platform.

The apparatus for denaturing and optionally removing any complementary nucleic acid strand could comprise apparatus for heating the platform to 94° C., or further syringe or peristaltic dispensers which dispense heated reagents or other denaturing chemicals.

In an alternative design, the rotatable platform does not necessarily need to be a disc per se; it could be comprised of a plurality of discrete reaction wells which are loaded into a cradle for holding each discrete reaction well in a rotary format. For example a modified 0 2 mL microfuge tube can be mounted at 45 degrees on a platform in the form of a rotatable cradle. In this configuration the cap is open and is on the horizontal plane (the inside surface of the cap facing upward). The cap is modified such that reagents dispensed into the cap at low rpm could be spun into the tube at high rpm. The plastic hinge of the microfuge tube is also modified to act as a channel to direct waste reagent from the cap to the tube. The cap would serve as the discrete area to perform the sequencing reaction and the tube itself would serve as the waste trough. The advantage is the operator could load one sample or many by inserting the desired number of tubes into the cradle.

Other aspects of the present invention relate to conducting sequencing of nucleic acid strands in parallel, i.e. multiplex sequencing. For example, the present invention provides a rotatable cylinder for conducting sequencing of a nucleic acid strand, said cylinder having at least one circumferentially extending lane, each said lane comprising one or more discrete areas adapted to immobilise a first binding partner or adapted to selectively immobilise a second binding partner. The skilled person will appreciate that this embodiment enables many samples to be run simultaneously or in parallel.

The skilled addressee will understand that the invention comprises the embodiments and features disclosed herein as well as all combinations and/or permeations of the disclosed embodiments and features.

BRIEF DESCRIPTION OF THE DRAWINGS

Preferred embodiments of the invention will now be described, by way of example only, with reference to the accompanying drawings in which: FIG. 1A is a plan view of the rotatable platform of the invention;

FIG. 1B is a side view of the rotatable platform shown in FIG. 1A;

FIG. 1C is sectional view taken on line 1C-1C of FIG. 1B;

FIG. 2A is a perspective view and FIG. 2B is a cut-away perspective view of an embodiment of the rotatable platform shown in FIG. 1;

FIG. 3A is a perspective view and FIG. 3B is a cut-away perspective view of an embodiment of the rotatable platform shown in FIG. 1;

FIGS. 4A and B are plan and side views respectively of an alternative embodiment of the rotatable platform shown in FIG. 1 and having a peripheral trough;

FIG. 5 is a sectional view of apparatus having the rotatable platform shown in FIG. 1A installed therein;

DEFINITIONS

Figure 6:
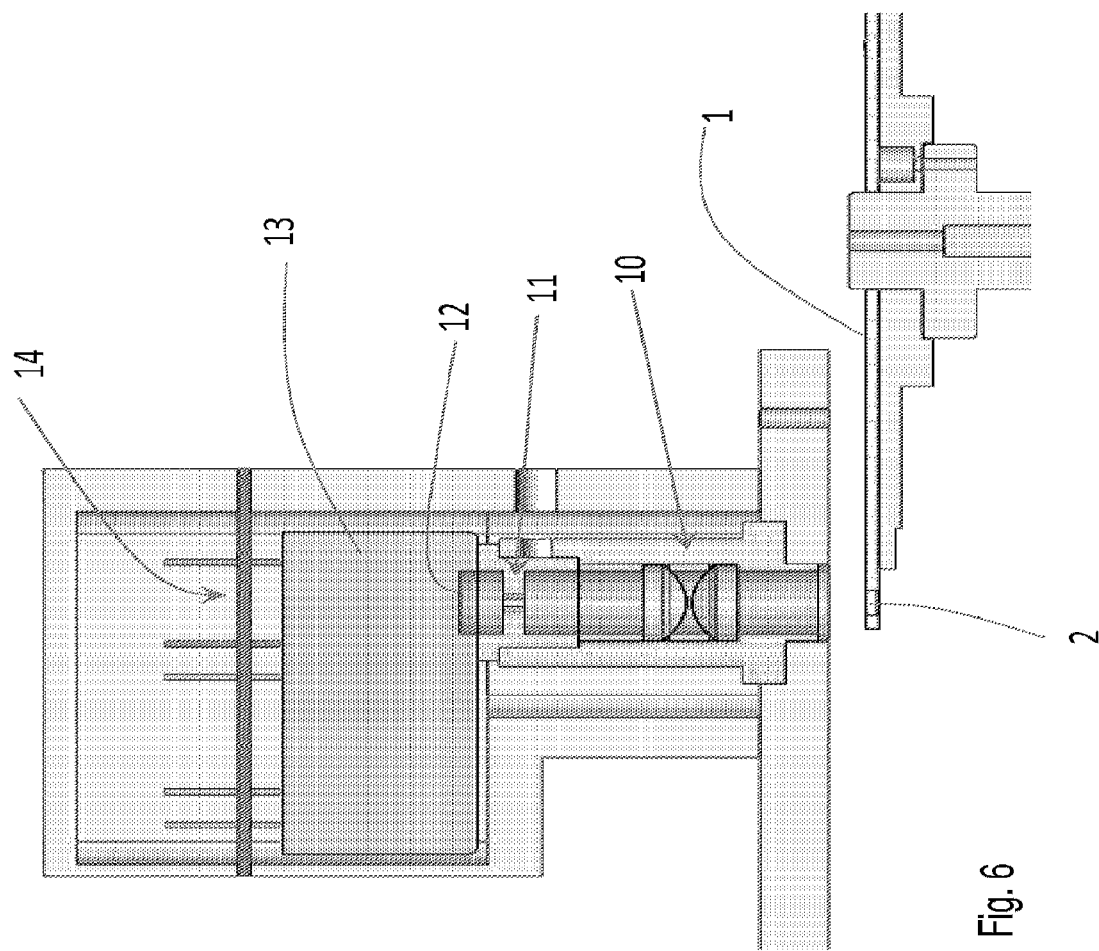
FIG. 6 shows optical detection apparatus utilising focussing optics for monitoring a reaction.

In describing and claiming the present invention, the following terminology will be used in accordance with the definitions set out below. It is also to be understood that the terminology used herein is for the purpose of describing particular embodiments of the invention only and is not intended to be limiting. Unless defined otherwise, all technical and scientific terms used herein have the same meaning as commonly understood by one having ordinary skill in the art to which the invention pertains.

Unless the context clearly requires otherwise, throughout the description and the claims, the words 'comprise', 'comprising', and the like are to be construed in an inclusive sense as opposed to an exclusive or exhaustive sense; that is to say, in the sense of 'including, but not limited to'.

In what follows, or where otherwise indicated, '%' will mean 'weight %', 'ratio' will mean 'weight ratio' and 'parts' will mean 'weight parts'.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

To provide a more concise description, some of the quantitative expressions given herein are not qualified with the term 'about'. It is understood that whether the term 'about' is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

The terms 'predominantly' and 'substantially' as used herein shall mean comprising more than 50% by weight, unless otherwise indicated.

The recitation of a numerical range using endpoints includes all numbers subsumed within that range (e.g., 1 to 5 includes 1, 1.5, 2, 2.75, 3, 3.80, 4, 5, etc.).

The terms 'preferred' and 'preferably' refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms 'a', 'an' and 'the' mean 'one or more', unless expressly specified otherwise. The terms 'an embodiment', 'embodiment', 'embodiments', 'the embodiment', 'the embodiments', 'an embodiment', 'some embodiments', 'an example embodiment', 'at least one embodiment', 'one or more embodiments' and 'one embodiment' mean 'one or more (but not necessarily all) embodiments of the present invention(s)' unless expressly specified otherwise The enumerated listing of items does not imply that any or all of the items are mutually exclusive. The enumerated listing of items does not imply that any or all of the items are collectively exhaustive of anything, unless expressly specified otherwise. The enumerated listing of items does not imply that the items are ordered in any manner according to the order in which they are enumerated.

Headings of sections provided in this patent application and the title of this patent application are for convenience only, and are not to be taken as limiting the disclosure in any way.

As used herein, the term 'binding partner' is understood to mean one of a binding partner pair, which can be any ligand/receptor pair. One of the binding partner pair is referred to as the "first binding partner" and the other of the binding partner pair is referred to as the "second binding partner". For example, the binding partner pairs can be streptavidin/avidin and biotin. The binding partner pairs can, for example, include streptavidin and biotinylated nucleic acid.

As used herein, the term 'rotatable' is intended to mean adapted to be rotated.

Preferred Embodiment of the Invention

Numerous embodiments are described in this patent application, and are presented for illustrative purposes only. The described embodiments are not intended to be limiting in any sense. The invention is widely applicable to numerous embodiments, as is readily apparent from the disclosure herein. These embodiments are described in sufficient detail to enable those skilled in the art to practice the invention, and it is to be understood that other embodiments may be utilized and that other changes may be made without departing from the scope of the present invention. Accordingly, those skilled in the art will recognize that the present invention may be practiced with various modifications and alterations. References will now be made to the drawings wherein like reference numerals refer to like parts throughout.

A preferred embodiment of the present invention will now be described with reference to pyrosequencing. Description of a preferred embodiment with reference to pyrosequencing should not be taken as limiting the invention to pyrosequencing assays.

Referring to FIG. 1, a rotatable platform in the form of a polycarbonate disc 1 is provided which comprises two or more discrete areas 2 adapted to selectively retain a nucleic acid strand for conducting sequencing of the nucleic acid. The discrete areas 2 are preferably about 2-3 mm in diameter, coated with streptavidin, and are positioned around the circumference of the disc 1 in equally spaced intervals. For example, a disc 1 having a diameter of 120 mm has a circumference of 377 mm, and by forming 3 mm diameter discrete areas 2 spaced apart by 6 mm (between centres of discrete areas/target sites 2) at radius of 55 mm from the centre of the disc 1 results in approximately 57 discrete areas around the periphery of the disc 1. However, the number of discrete areas could be a smaller or greater number by using either a larger disc 1 or smaller discrete areas, e.g. 0.5 mm diameter with a spacing of, say, 1 mm, or any combination thereof.

Preferably the discrete areas 2 are shallow wells, which comprise a volume of between about 0.5 to 100 µL.

Other embodiments can be seen in FIGS. 2 and 3, in which like features have been given like reference numerals. In these examples, the rotatable platforms are 120 mm in diameter with 50 wells equally spaced around the periphery. The wells are about 3 mm in diameter, and can be fabricated from materials including polycarbonate, clear polystyrene and white high impact polystyrene (HIPS). Platform thicknesses are typically 1 mm to 3 mm, and well depths of 0.8 mm to 2.8 mm.

In some embodiments, as best shown in FIG. 4, the rotatable platform 1 further comprises a trough 3 disposed at the periphery of the platform for receiving waste fluids which are spun off or centrifuged away from the surface of the rotatable platform 1 during its rotation. Preferably the trough 3 is a moulded element of the platform 1. It will be appreciated that with each step in the sequencing reaction waste reagents are centrifuged off the platform, and in order to improve the handling of the waste fluids a trough 3 is provided. However, in an alternative embodiment the housing 4 within which the rotatable platform 1 is positioned can be configured to have a trough 5 disposed adjacent the periphery of the platform 1 to receive waste fluids which are spun off the surface of the rotatable platform 1 during its rotation. The fluids in the trough 5 can be extracted through a conduit 6 away from the platform 1 in order to minimise contamination. Preferably a vacuum system is used (not shown).

The sequencing method preferably employed is pyrosequencing. However, it will be appreciated that other methods of sequencing a nucleic acid strand may be utilised, as discussed previously.

Preferably the discrete areas 2 are adapted to selectively immobilise the nucleic acid strand. For example, the nucleic acid strand may be biotinylated and the discrete areas 2 comprise streptavidin for binding the biotinylated nucleic acid strand thereto. However, it will be appreciated that other chemistries are available for immobilising a nucleic acid strand to a discrete area 2.

According to a method of the invention for conducting sequencing of a nucleic acid strand, a rotatable platform 1 is provided and the nucleic acid strand is immobilised to the discrete areas 2. Any complementary nucleic acid strand is then denatured and removed, for example by heating the platform 1 to about/approximately 94° C. The discrete area 2 is then contacted sequentially with A, T, G and C nucleotides, wherein between each contacting step the platform 1 is rotated such that any residual or unreacted nucleotide is substantially centrifugally removed from the discrete areas 2.

The method of the invention further comprises the step of analysing the nucleic acid strand during and/or after each said contacting step. The analysis step comprises detecting the next base pair in the nucleic acid strand by correlating the output of light resulting from the incorporation of nucleotide with the number of nucleotides which have become bound to the nucleic acid strand. A suitable detector for detecting the light produced by the reaction is a photomultiplier. It will be appreciated that as the rotatable platform 1 is rotated all the samples pass the detector. If no nucleotide is incorporated then there is no light signal and the reaction mixture is spun off (either every cycle or every 10-50th cycle (say) but less than the 80th cycle) using centrifugal force, and another round is commenced with the next nucleotide.

In preferred embodiments, prior to contacting the discrete areas 2 with a subsequent nucleotide each target site 2 is subjected to a washing or rinsing step with a washing reagent. The washing reagent may be any reagent which can substantially wash off any residual solution from the previous contacting step, and is preferably a PCR buffer.

Preferably the rotatable platform 1 is rotated at low speed whilst dispensing the nucleotide reagents and enzyme, for example at between about 10 to 200 rpm, and the platform 1 is rotated at high speed whilst dispensing the washing reagent, for example at between about 400 to 1000 rpm.

The present invention provides use of the rotatable platform 1 for sequencing a nucleic acid strand, and a kit comprising the rotatable platform 1 and one or more reagents for sequencing the nucleic acid strand.

Referring to FIG. 5, the present invention also provides apparatus for use with the rotatable platform 1 for sequencing a nucleic acid strand. The apparatus comprises a motor for rotating the platform 1 at a predetermined controllable user-selectable rotational speed, such as a motor capable of delivering rotational speeds of between about 10 to 1000 rpm. Apparatus is also provided for dispensing the nucleic acid strand onto the discrete areas 2 for immobilising the nucleic acid strand to the discrete areas 2. Such apparatus may take the form of ink jet-type technology or a suitable dispenser 7 such as a syringe pump. Apparatus is also provided for dispensing A, T, G and C nucleotides into contact with the discrete areas 2 and for dispensing a washing reagent. Again, such apparatus may take the form of ink jet-type technology. Apparatus is also provided for denaturing and removing any complementary nucleic acid strand, and such apparatus may take the form of a heating coil (not shown in this Figure) disposed within the housing 4.

Figure 7:
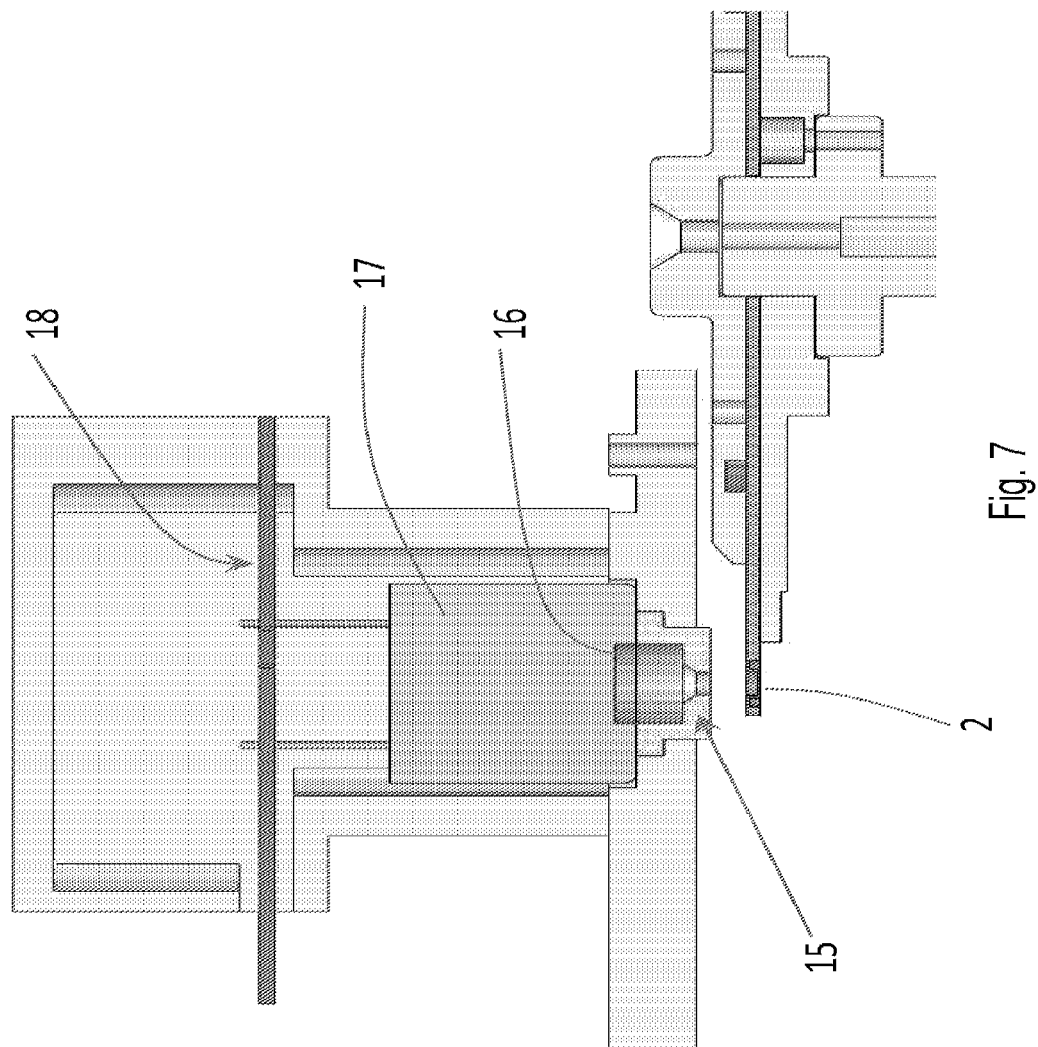
FIG. 7 shows optical detection apparatus utilising direct imaging for monitoring a reaction.

A suitable detector 8 is also provided to detect light produced by the pyrosequencing reaction. Suitable detectors will be known to the skilled person, for example a photomultiplier which may be mounted beneath or above the rotatable platform 1. Particular reference is now made to FIGS. 6 and 7 which show various embodiments of photomultiplier detectors for use in the invention. One optical configuration uses focusing optics (FIG. 6) and the second uses direct imaging (FIG. 7). FIG. 6 details a focussing lens 10, an aperture 11, a photosensitive surface 12, a photomultiplier 13 and detection electronics 14. FIG. 7 details an aperture 15, a photosensitive surface 16, a photomultiplier detector 17 and detection electronics 18.

Figure 8:
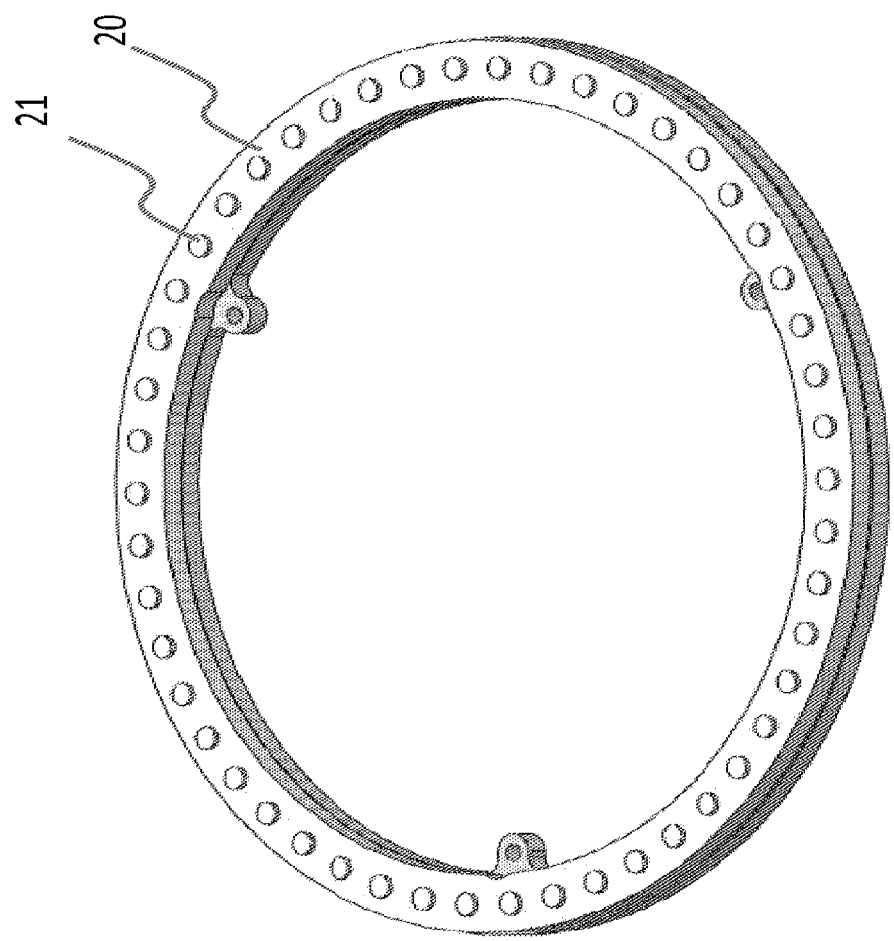
FIG. 8 shows a heater ring for heating the discrete areas on the platform.
Figure 9:
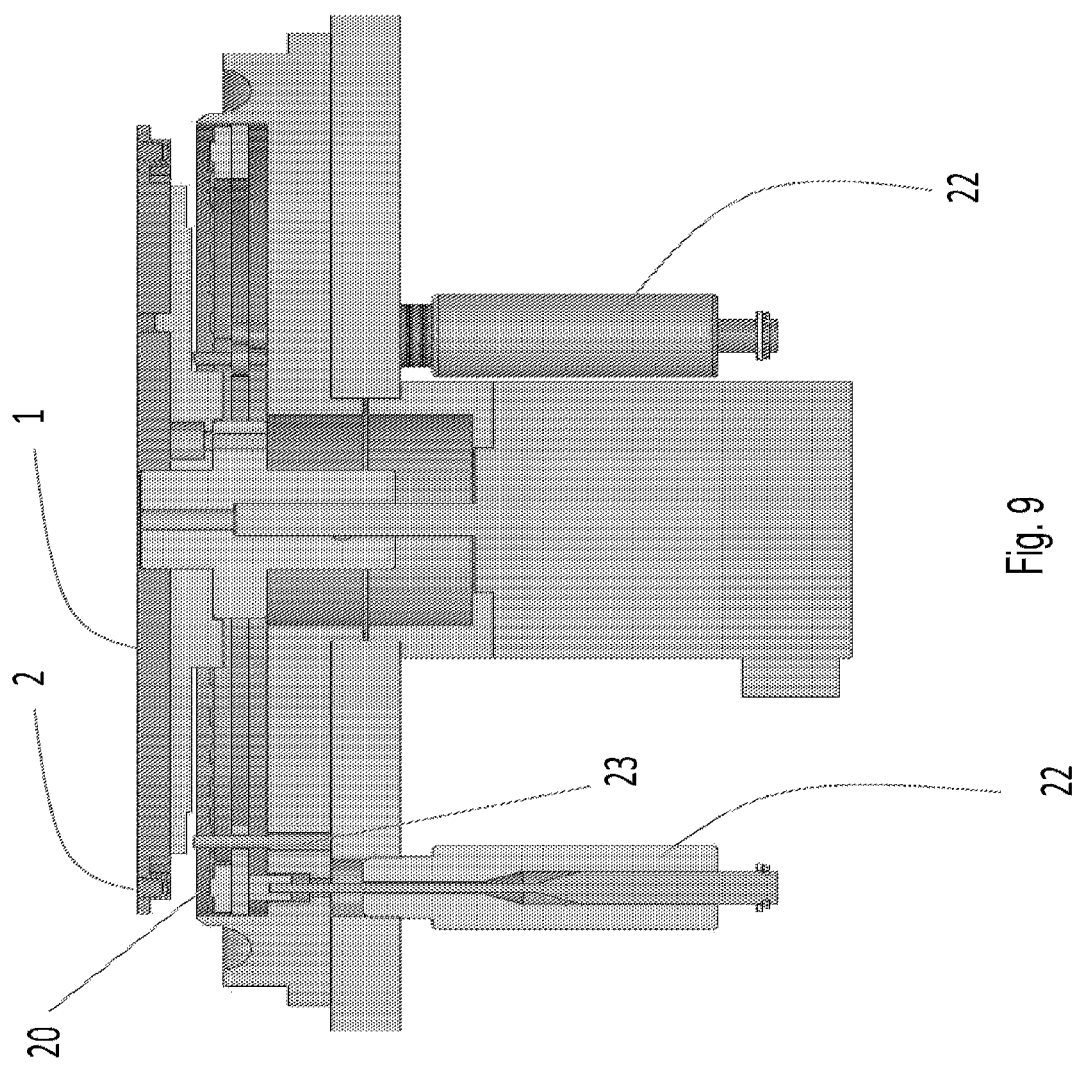
FIG. 9 shows apparatus incorporating the heater ring shown in FIG. 8.

Referring now to FIG. 8, a heating coil or ring 20 is shown. The heater ring 20 consists of an aluminium ring bonded to a heater PCB (printed circuit board). The heater PCB incorporates temperature sensing element (not shown) to allow closed loop control of the heater temperature. The heater ring 20 may or may not have the projections 21 on the surface depending on the design of the wells/discrete areas on the rotatable platform 1. The projections 21 are designed to ensure only the bottom of the wells in the rotatable platform contact the heater ring 20. The heater ring 20 is preferably designed to move up to contact the rotatable platform 1, and move down to allow the rotatable platform 1 to rotate freely, and to quickly remove the heat from the reaction well. This may be achieved using solenoids 22 to slide the heater ring 20 up and down guide posts 23.

The rotatable platform 1 can be rotated a low speed to dispense the enzyme and nucleotide(s) mixture (i.e. 200 rpm or less) where the centrifugal force is low enough not to move the mixture from the discrete areas 2 and to allowing for the reaction to proceed and optical detection to be completed. Wash reagents can be added at high rotor speed, (i.e. 400 rpm) so the wash removes all reagents from the target sites 2 and does not substantially contaminate between discrete areas 2.

Figure 10:
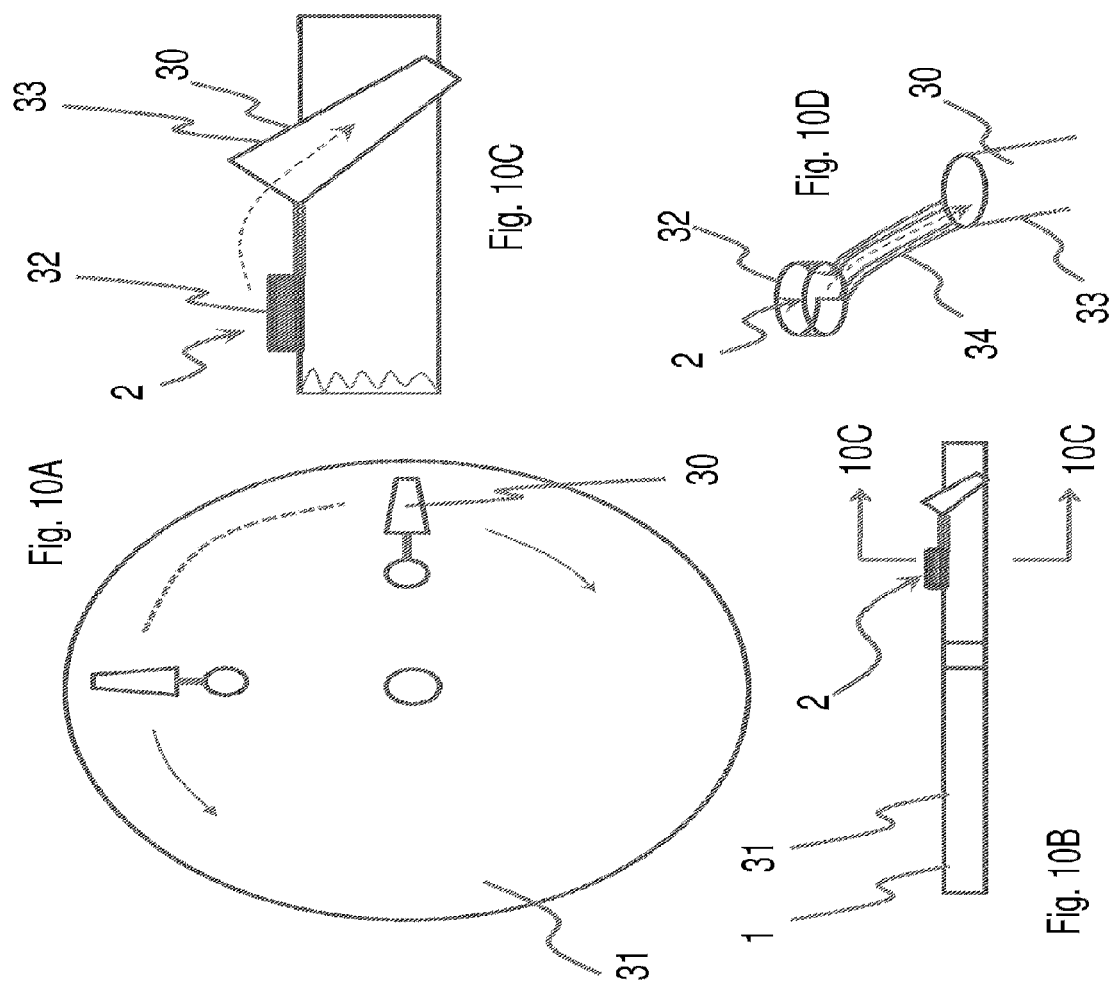
FIG. 10A is a plan view of the rotatable platform in the form of a cradle adapted to receive at least one microcentrifuge tube for conducting sequencing of nucleic acid.
FIG. 10B is a side view of the rotatable cradle shown in FIG. 4A.
FIG. 10C is sectional view taken on line 10C-10C of FIG. 10B.
FIG. 10D is perspective view of a modified microfuge tube for use with rotatable platform of the invention which is in the form of a rotatable cradle.

Turning now to FIGS. 10A to 10C, in an alternative design the rotatable platform 1 does not necessarily need to be a disc per se; it could be comprised of a plurality of discrete reaction wells 30 which are loaded into a cradle 31 for holding each discrete reaction well 30 in a rotary format. For example, the discrete reaction wells 30 may be in the form of a modified 0.2 mL microfuge tube which can be mounted at 45 degrees on a platform 1 in the form of a rotatable cradle 31. In this configuration the cap 32 is open and is on the horizontal plane (the inside surface of the cap facing upward). The cap 32 is modified such that reagents dispensed into the cap at low rpm could be spun into the tube 33 at high rpm (see dotted arrow). The cap 32 serves as the target site 2 to perform the sequencing reaction and the tube 33 itself serves as the waste trough 3. The hinge 34 may be modified to act as a channel to transport the centrifuged waste reagents to the tube 33.

EXAMPLES

As discussed above, the determination of a DNA sequence can be achieved through the use of the Pyrosequencing application (see Agah A., Aghajan M., Mashayekhi F., Amini S., Davis R., Plummer J. D., Ronaghi M., Griffin P. B., *A multi-enzyme model for pyrosequencing, Nucleic Acids Res.*, 2004; 32: e166). Sequencing is achieved by detecting the release of pyrophosphate following the incorporation of a complementary three prime deoxyribonucleoside five prime triphosphate (dNTP) into a single stranded template by the DNA polymerase enzyme. Initially, the pyrophosphate must be converted to adenosine triphosphate (ATP) by the sulfurylase enzyme. It is the reaction of ATP with luciferin through the luciferase enzyme that generates a light signal, indicating the incorporation of the nucleotide and hence, the sequence of the template strand. To allow for the incorporation and detection of the next nucleotide without interference from the previously added nucleotide, the apyrase enzyme is used. Apyrase will degrade excess nucleotide prior to the addition of the next nucleotide.

During the process of pyrosequencing there is an accumulation of by-products such as sulphate and diphosphate nucleotides. These by-products inhibit the enzymes resulting in a reduction in signal quality during a long sequence run. For example, inhibition of the apyrase results in a reduction in the removal of unincorporated nucleotides that leads to non-synchronised incorporation of bases and thus poor signal detection. As a result the length of sequencing using the pyrosequencing application is currently limited to no more than 60 nucleotides (see Mashayekhi F., Ronaghi M., *Analysis of read-length limiting factors in pyrosequencing chemistry, Anal. Biochem.*, 2007; 363: 275-287).

Therefore, in order to reduce the effects of by-product inhibition, and increase read length, the present invention enables the reaction components to be washed away after a number of nucleotide exposures, allowing fresh reagent to be added to continue the next section of the sequence, while ensuring the template remains bound to the support.

Sequencing Target

A five prime biotin labelled synthetic oligonucleotide with a self priming loop sequence (highlighted in underline) was used to achieve up to 30 base pair sequencing on a platform according to the invention. The complete base pair sequence for the synthetic oligonucleotide (SEQ-OLIGO-30BP) was;

5'-Biotin- A G T G T G C A GG A C G A G T CCCC A CC A C A CCC

<u>AGGAAACAGCTATGACCATGCTTGCATGGTCATAGCTGTTTCC</u>-3'

The self priming loop sequence allowed the pyrosequencing reaction to commence from the 3' end of the synthetic oligonucleotide as it folds over its complementary sequences. Therefore, the first nucleotide to be recognised by the reaction was the adenosine (A) base, highlighted in bold. As a result, the first nucleotide used in the reaction sequence was the complementary nucleotide, thymidine (dTTP). Hence the complete sequence for SEQ-OLIGO-30BP reaction was: T GGG T G T GG T GGGG A C T C G T CC T G C A C A C T. As the pyrosequencing reaction can recognise heteropolymer nucleotides (multiple stretches of the same nucleotide), the actual dispensation order of nucleotides for sequencing was shorted to: T G T G T G T G A C T C G T C T G C A C A C T. The SEQ-OLIGO-30BP oligonucleotide was diluted down to a concentration of 0.2 micro molar.

Streptavidin Coated Discs

High impact polystyrene discs were coated with streptavidin through a covalent linkage between the protein and polymer using the chemical 1-Ethyl-3-(3-dimethylaminopropyl) carbodiimide hydrochloric acid (EDC). Wells were prepared by adding 2.5 micro litres of EDC at a concentration of 10 milligrams per millilitre and 2.5 micro litres of streptavidin at a concentration of 5 milligrams per millilitre, then incubating for 4 hours at room temperature in a humidity box to reduce evaporation of the reaction. Following incubation, the wells were washed with phosphate buffered saline and then water. The wells were allowed to air dry for 1 hour and were then stored at 4° C. in sealed bags containing desiccant.

Figure 11:
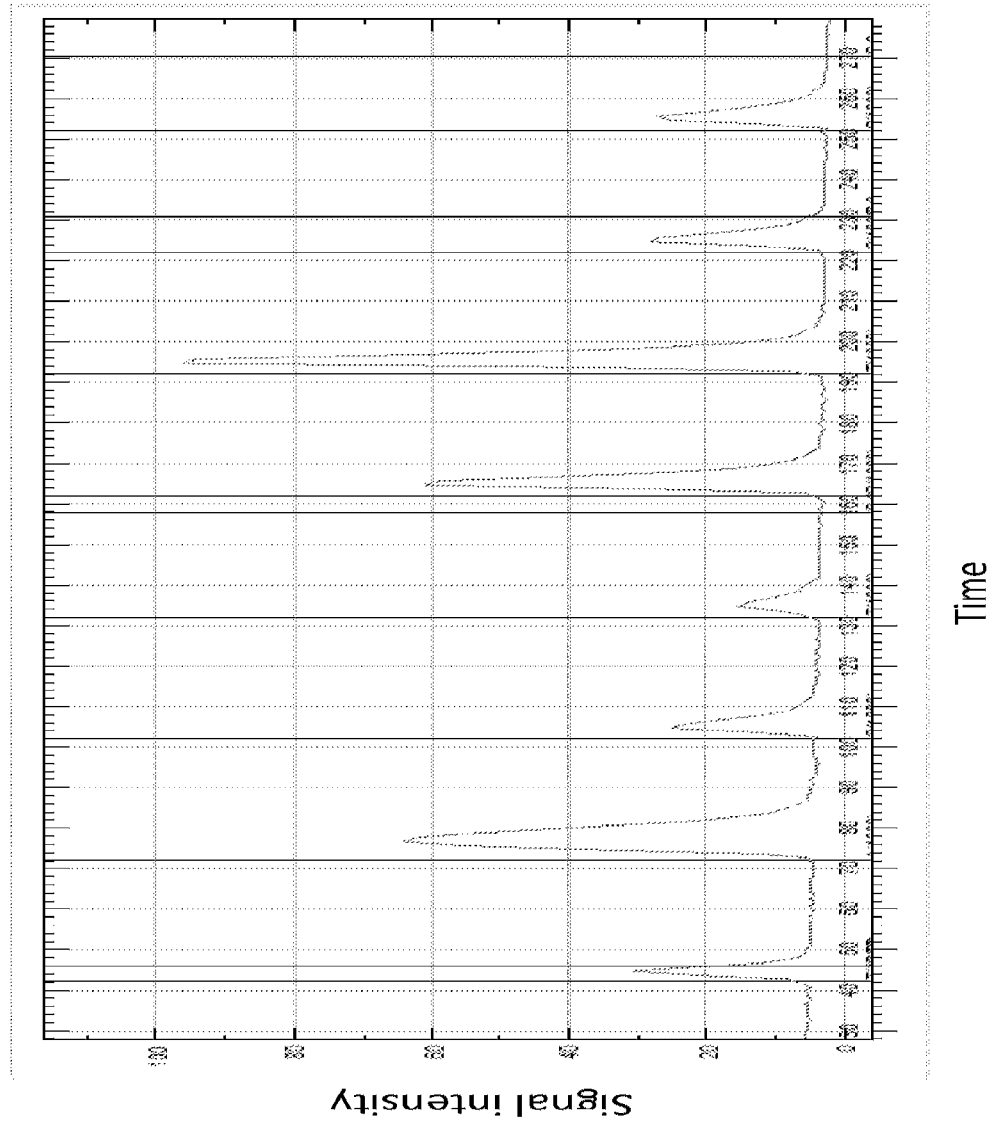
FIG. 11 is a pyrogram result for a polystyrene well coated with streptavidin in the presence of EDC.

The ability to covalently bind the streptavidin to the polystyrene platforms was demonstrated by running a number of control experiments using a control oligonucleotide provided by QIAGEN GmbH. Sequencing of the control oligonucleotide was achieved as described below without a wash step. The sequence of the control oligonucleotide was T A (C or T) G G T T T G C, with the order of nucleotide dispensation being T A C T G T G C. The control wells where either absent in EDC or Streptavidin. Pyrosequencing of the positive disc demonstrated good strong signals (FIG. 11). No real signal was observed for either the streptavidin negative or EDC negative controls (FIGS. 12 and 13).

The Pyrogram result for a polystyrene well coated with streptavidin in the presence of EDC are shown in FIG. 11. The result demonstrates that the template had bound to the vessel through a biotin-streptavidin bond allowing sequence identification.

Figure 12:
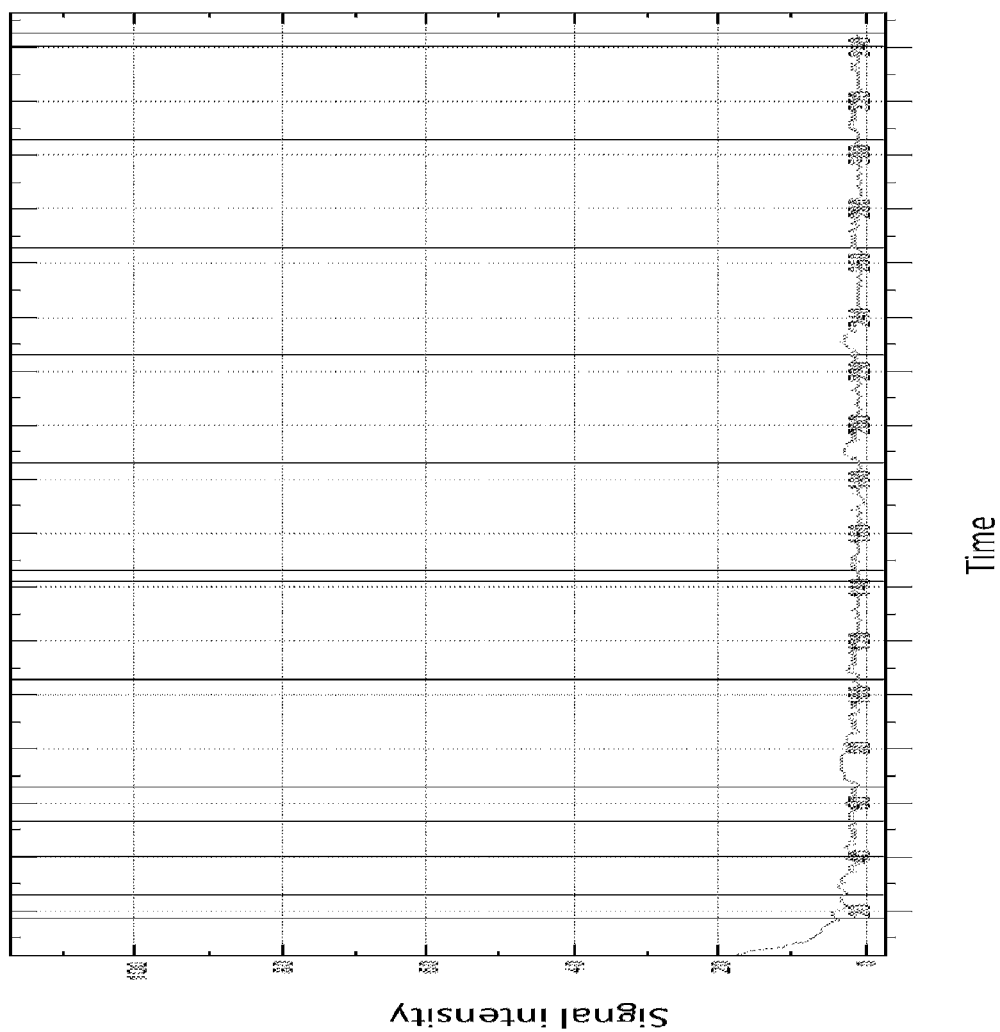
FIG. 12 is a pyrogram for the streptavidin negative control well demonstrating that only template bound to streptavidin could have generated signal.

The Pyrogram result for the streptavidin negative control shown in FIG. 12 demonstrates that only template bound to streptavidin could have generated signal. Therefore, no signal was contributed by residual template post wash in the result for FIG. 11.

Figure 13:
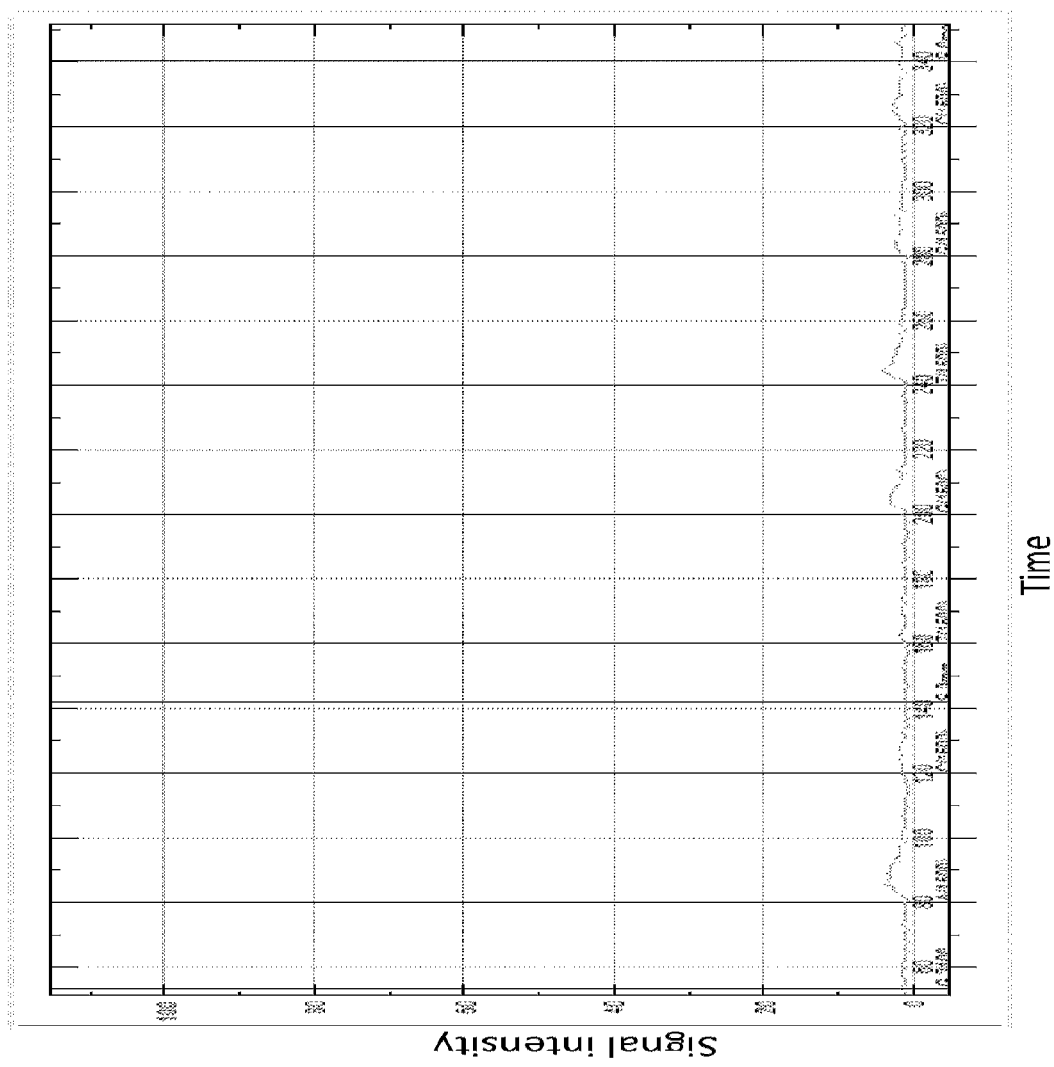
FIG. 13 is a pyrogram for EDC negative control well showing no signal during sequencing.

Pyrogram result for EDC negative control is shown in FIG. 13, showing no signal during sequencing. The result demonstrated that streptavidin was only bound to the polystyrene well in the presence of EDC. Therefore, binding to the platform was achieved using covalent bonding.

Assay Setup

Five micro litres of the oligonucleotide was aliquoted into a well of a covalently bonded streptavidin coated polystyrene disc/platform to provide 1 pico mole of target for sequencing. The template was incubated for 10 min at room temperature to allow for biotin-streptavidin binding to occur. Following incubation, any unbound template was pipetted off and the well washed twice with 5 micro litres of deionised water to ensure any residual unbound template was removed.

Sequence-Wash-Sequence

The disc 1 was positioned into the instrument. The run was manually setup to allow for the microinjection of 2 micro litres of water, 1 micro litre of the enzyme mix that included DNA polymerse, sulfurylase, luciferase and apyrase, and 1 micro litre of substrate that consisted of luciferin and buffer. Following a 10 second period to allow for baseline stabilisation, post enzyme and substrate addition, a negative control nucleotide, dGTP, was microinjected at 100 nano litres to ensure that no random signals were being generated during the run. As the guanosine nucleotide is not the first base in the sequence it should not generate a signal peak on addition. The next set of nucleotides was loaded at 100 nano litres at 30 second intervals using the following dispensation order: TGTGTGT. The correct addition of each nucleotide resulted in a light signal peak. The peak value depended on the number of the same nucleotide in a row. The resulting graph of these peaks is referred to as a pyrogram.

Following the addition of these eight nucleotides, the reaction content was spun off by rotating the disc at 1000 revolutions per minute for 5 seconds. At the completion of the high speed rotation, the rotor speed was reduced back to 60 revolutions per minute and the cycle for sequencing recommenced by adding the same volumes of water, enzyme and substrate. Subsequently, the next set of nucleotides was then loaded and signal peaks measured. The second and third sets of nucleotides used were: G A C T C G T C and T G <u>T</u> C A C A T, with the underlined nucleotide used as a further negative control to monitor for reaction nonspecificity. A wash step was applied between the two sets of sequences. The complete sequence data can be seen in FIG. 14.

Figure 14:
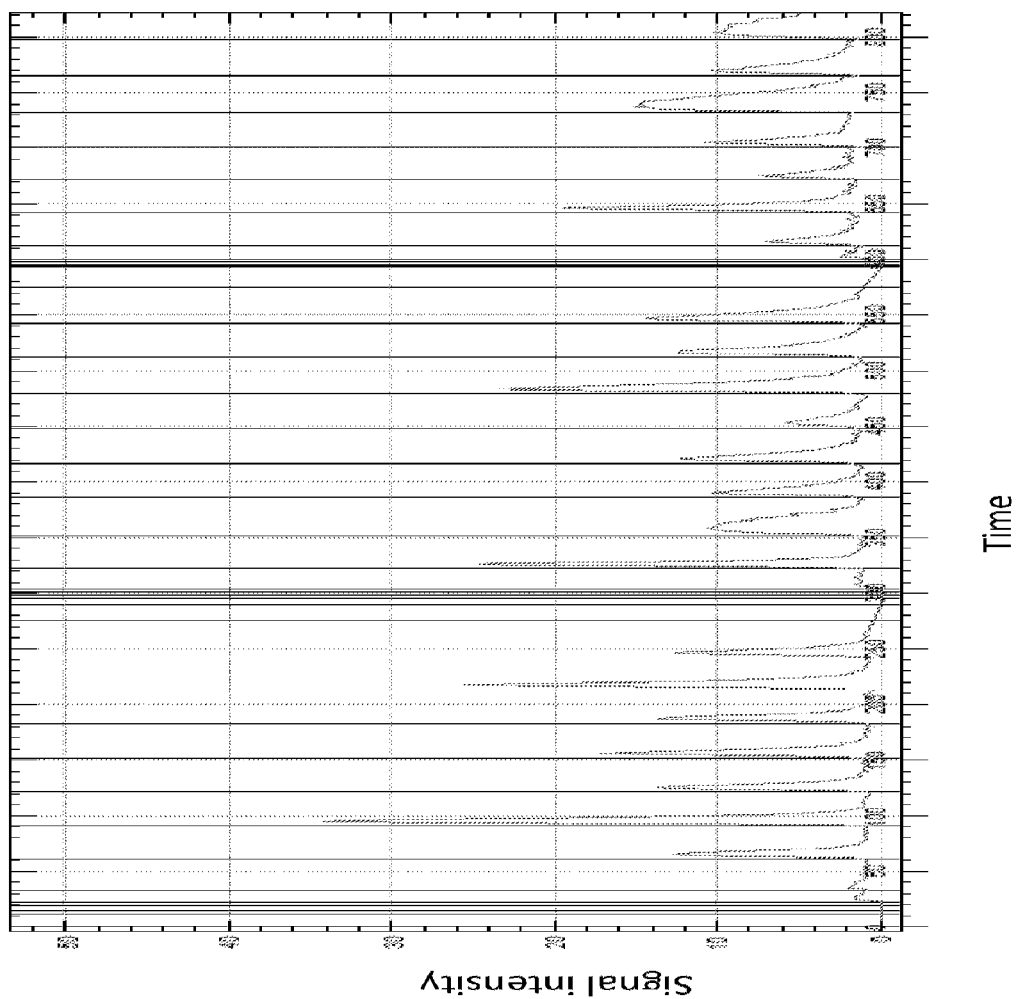
FIG. 14 is a pyrogram of the SEQ-OLIGO-30BP synthetic oligonucleotide sequence using a sequence-wash-sequence strategy.

FIG. 14 shows a Pyrogram of the SEQ-OLIGO-30BP synthetic oligonucleotide sequence using a sequence-wash-sequence strategy. The five prime, biotin labelled, SEQ-OLIGO-30BP template with self priming loop sequence was loaded into the well of a streptavidin coated high impact polystyrene disc to allow for biotin-streptavidin binding to capture the target to the well. Any unbound template was washed and the sequence reaction commenced with the addition of enzyme and substrate. A negative control nucleotide (dGTP) was loaded first to monitor for nonspecificity in the reaction. Seven of the first nucleotides of the known sequence were microinjected at 100 nano litre volumes at 30 second intervals. Peaks were generated for each of the corresponding bases in the sequence. Peak values varied depending on the run of the same nucleotide within the sequence. At the addition of all the nucleotides of the first set, the rotor speed was increased to 1000 revolutions per minute to remove the liquid contents of the well, leaving the template in place bound to the streptavidin coated disc. After five seconds the speed was reduced back to 60 revolutions per minute and the sequence process recommenced by the addition of new enzyme and substrate and the next set of nucleotides. The result demonstrates the ability of the sequence-wash-sequence on streptavidin coated discs of the invention.

Whereas this invention is illustrated and described with reference to embodiments presently contemplated as the best modes or modes of carrying out such invention in actual practice, it is to be understood that various changes may be made in adapting the invention to different embodiments without departing from the broader inventive concepts disclosed herein and comprehended by the claims that follow.

The claims defining the invention are as follows:

1. A method of pyrosequencing a polynucleotide molecule, said method comprising the steps of:

providing a rotatable platform adapted to bind a polynucleotide molecule in one or more discrete uncovered areas on an upper surface of said rotatable platform;

binding said polynucleotide molecule to one or more of said discrete uncovered areas on said upper surface of said rotatable platform;

annealing an oligonucleotide primer to a single strand of said polynucleotide molecule; and dispensing onto each said discrete uncovered area from a point external of said platform a series of pyrosequencing reagents, wherein after one or more or all of said dispensing steps said platform is rotated sufficiently such that any residual or unreacted said reagent is substantially centrifugally removed from each discrete area and off said platform;

assaying for the presence of a pyrophosphate group; and repeating said dispensing and assaying steps, thereby sequencing said polynucleotide molecule.

2. A method according to claim 1, wherein said rotatable platform is substantially circular, and wherein about 2 to 500 discrete uncovered areas are distributed about the periphery of the upper surface of said circular platform.

3. A method according to claim 1 or 2, wherein the diameter of said rotatable platform is between about 50 to 500 mm, the thickness of said platform is about 1 to 4 mm, and wherein said discrete uncovered areas are substantially flat or are substantially shallow wells comprising a volume of between about 0.5 to 100 μL or a well depth of about 0.5 to 3 mm.

4. A method according to claim 1, wherein said rotatable platform is formed of a plastics material selected from the group consisting of polycarbonate, polystyrene, high impact polystyrene, polyethylene and polypropylene, or is formed from glass or quartz.

5. A method according to claim 1, wherein said one or more discrete uncovered areas are a coating on said rotatable platform, wherein said coating is adapted to bind said polynucleotide molecule.

6. A method according to claim 1, wherein said polynucleotide molecule is chemically adsorbed or covalently or ionically, or hydrogen bonded onto each said discrete uncovered area of said platform, or van der Waals forces bind said polynucleotide molecule to each said discrete uncovered area of said platform.

7. A method according to claim 1, wherein said rotatable platform comprises a trough disposed at the periphery of said rotatable platform for receiving waste fluids which are spun off or centrifuged away from the upper surface of said rotatable platform during its rotation.

8. A method according to claim 1, wherein said pyrosequencing reagents are selected from the group consisting of: one or more enzymes, substrates, A, T, G and/or C nucleotides or the respective suitable nucleotide analogs, washing reagents and rinsing reagents.

9. A method according to claim 1, wherein the step of rotating the rotatable platform is performed at a speed of about 400 to 1000 rpm to substantially centrifugally remove said residual or said unreacted reagents off the upper surface of said platform, and further comprising the step of rotating the rotatable platform at a speed of about 10 to 200 rpm whilst dispensing said reagent.

10. A method according to claim 1 wherein said polynucleotide molecule is DNA or RNA or a modified form thereof.

11. A method according to claim 1 wherein said polynucleotide molecule is biotinylated and said discrete area(s) comprises avidin or streptavidin or an analogue for binding the biotinylated polynucleotide molecule.

12. A method according to claim 1 wherein said dispensing of the series of pyrosequencing reagents comprises either:
 a) adding each nucleotide or its analog separately and sequentially in any desired or predetermined order, or
 b) adding A+T+G+C nucleotides or any predetermined or desired subset of these as a mixture, and optionally repeating the adding one or more times.

13. A method according to claim 1 wherein said assaying for the presence of a pyrophosphate group comprises detecting a light signal.

14. A method according to claim 1 wherein the polynucleotide molecule is a double stranded polynucleotide molecule and the method further comprises denaturing the double stranded polynucleotide molecule prior to the annealing step and centrifugally removing the unbound strand after denaturation.

15. A method according to claim 14 wherein said denaturing comprises heating said double stranded polynucleotide molecule to effect denaturing, or exposing said double stranded polynucleotide molecule to elevated pH.

16. A method according to claim 1 further comprising the step of washing said discrete uncovered area(s) with a wash reagent and optionally an enzymatic treatment.

17. A method according to claim 16 wherein said washing step occurs after one or more dispensing steps.

18. A method according to claim 8 wherein said enzymes include one or more of DNA polymerase, ATP sulfurylase, luciferase and apyrase.

19. A method according to claim 8 wherein said substrates include adenosine 5' phosphosulfate (APS) and/or luciferin.

* * * * *

SEQUENCE LISTING

```
<160> NUMBER OF SEQ ID NOS: 4

<210> SEQ ID NO 1
<211> LENGTH: 72
<212> TYPE: DNA
<213> ORGANISM: Artificial Sequence
<220> FEATURE:
<223> OTHER INFORMATION: chemically-synthesized oligonucleotide with
      self-priming loop

<400> SEQUENCE: 1
agtgtgcagg acgagtcccc accacaccca ggaaacagct atgaccatgc ttgcatggtc      60
atagctgttt cc                                                          72

<210> SEQ ID NO 2
<211> LENGTH: 30
<212> TYPE: DNA
<213> ORGANISM: Artificial Sequence
<220> FEATURE:
<223> OTHER INFORMATION: chemically-synthesized sequening product

<400> SEQUENCE: 2
tgggtgtggt ggggactcgt cctgcacact                                       30

<210> SEQ ID NO 3
<211> LENGTH: 23
<212> TYPE: DNA
<213> ORGANISM: Artificial Sequence
<220> FEATURE:
<223> OTHER INFORMATION: chemically-synthesized sequening product

<400> SEQUENCE: 3
tgtgtgtgac tcgtctgcac act                                              23

<210> SEQ ID NO 4
<211> LENGTH: 10
<212> TYPE: DNA
<213> ORGANISM: Artificial Sequence
<220> FEATURE:
<223> OTHER INFORMATION: chemically-synthesized oligonucleotide control

<400> SEQUENCE: 4 tayggtttgc                                                             10
```